United States Patent
Mohapatra et al.

(10) Patent No.: US 9,433,682 B2
(45) Date of Patent: Sep. 6, 2016

(54) GRAPHENE HYDROGEL AND METHOD FOR USING THE SAME

(71) Applicants: Subhra Mohapatra, Tampa, FL (US); Chunyan Wang, Tampa, FL (US)

(72) Inventors: Subhra Mohapatra, Tampa, FL (US); Chunyan Wang, Tampa, FL (US)

(73) Assignees: University South Florida, Tampa, FL (US); National Institutes of Health (NIH), U.S. Dept. of Health and Human Services (DHHS), Washington, DC (US)

( * ) Notice: Subject to any disclaimer, the term of this patent is extended or adjusted under 35 U.S.C. 154(b) by 0 days.

(21) Appl. No.: 13/775,560

(22) Filed: Feb. 25, 2013

(65) Prior Publication Data

US 2013/0230496 A1 Sep. 5, 2013

Related U.S. Application Data

(60) Provisional application No. 61/602,352, filed on Feb. 23, 2012, provisional application No. 61/602,378, filed on Feb. 23, 2012.

(51) Int. Cl.
| | |
|---|---|
| A01N 63/00 | (2006.01) |
| A01N 65/00 | (2009.01) |
| A61K 47/36 | (2006.01) |
| A61K 9/51 | (2006.01) |
| A61L 27/44 | (2006.01) |
| A61L 27/52 | (2006.01) |
| A61L 15/44 | (2006.01) |
| A61L 15/46 | (2006.01) |
| A61L 15/60 | (2006.01) |
| C12N 5/00 | (2006.01) |
| C08B 37/08 | (2006.01) |
| C08L 5/08 | (2006.01) |
| C08J 3/075 | (2006.01) |
| C08F 292/00 | (2006.01) |

(Continued)

(52) U.S. Cl.
CPC .............. *A61K 47/36* (2013.01); *A61K 9/5161* (2013.01); *A61L 15/44* (2013.01); *A61L 15/46* (2013.01); *A61L 15/60* (2013.01); *A61L 27/443* (2013.01); *A61L 27/52* (2013.01); *C08B 37/003* (2013.01); *C08F 251/00* (2013.01); *C08F 290/062* (2013.01); *C08F 292/00* (2013.01); *C08J 3/075* (2013.01); *C08L 5/08* (2013.01); *C12N 5/0068* (2013.01); *C08F 220/54* (2013.01); *C08F 222/1006* (2013.01); *C08G 83/001* (2013.01); *C08J 2387/00* (2013.01); *C12N 2533/20* (2013.01); *C12N 2533/72* (2013.01)

(58) Field of Classification Search
None
See application file for complete search history.

(56) References Cited

U.S. PATENT DOCUMENTS

2009/0047331 A1* 2/2009 Kim et al. ............... 424/445
2009/0087493 A1* 4/2009 Dai et al. ................. 424/490

OTHER PUBLICATIONS

Ma et al., Carb. Poly., 79:620-627 (2010).*

(Continued)

*Primary Examiner* — Thomas J Visone
(74) *Attorney, Agent, or Firm* — Thomas | Horstemeyer, LLP

(57) ABSTRACT

Provided herein is a hydrogel composition comprising a graphene, a chitosan, and a polyethylene (glycol) diacrylate (PEGDA) (PCG hydrogel). In some embodiments, the hydrogel further comprises a N-isopropylacrylamide (NIPAM) (TPCG hydrogel). Also provided is a method for differentiating a mesenchymal stem cell comprising contacting the cell with the PCG hydrogel. Further provided herein is a method for delivering a pharmaceutical composition to a cell comprising administering to the cell a TPCG hydrogel and the pharmaceutical composition.

19 Claims, 18 Drawing Sheets

(51) Int. Cl.
  *C08F 251/00* (2006.01)
  *C08F 290/06* (2006.01)
  *C08F 220/54* (2006.01)
  *C08F 222/10* (2006.01)
  *C08G 83/00* (2006.01)

(56) References Cited

OTHER PUBLICATIONS

Fan et al., Biomacro., 11:2345-2351 (2010).*
Zhang et al, Polymer, 46:9664-9673 (2005).*
Yang et al., ACS App. Mater. Inter., 2(6):1707-1713 (2010).*
Depan et al., Acta Biomater., 7:3432-3445 (2011).*
Guo et al (J. Biosci. Bioeng., 6:547-556 (2007).*
Sun et al., Nano. Res., 1(3): 203-212 (2008).*
Berger et al., Euro. J. Phara. Biopharma., 57:19-34 (2004).*
Rana et al., Macromol. Mater. Eng., 296:131-140 (2011).*
Sun et al., Nano. Res., 1(3):203-212 (2008).*
Bhattarai et al., J. Control. Release, 103:609-624 (2005).*
Alvarez-Lorenzo, et al., "Light-Sensitive Intelligent Drug Delivery Systems", Photochemistry and Photobiology, vol. 85, pp. 848-860, 2009.
Bao HQ, et al., "Chitosan-Functionalized Graphene Oxide as a Nanocarrier for Drug and Gene Delivery", Small, vol. 7, pp. 1569-1578, (2011).
Yunqiang Chen, et al, "Graphene oxide—chitosan composite hydrogels as broad-spectrum adsorbents for water purification", J. Mater. Chem A., vol. 1, pp. 1992-2001 (2013).
D. Dapan, et al., "Structure—process—property relationship of the polar graphene oxide-mediated cellular response and stimulated growth of osteoblasts on hybrid chitosan network structure nanocomposite scaffolds", Acta Biomaterialia, vol. 7, pp. 3432-3445 (2011).
Hailong Fan, et al., "Fabrication, Mechanical Properties, and Biocompatibility of Graphene-Reinforced Chitosan Composites", Biomacromolecules, vol. 11, pp. 2345-2351 (2010).
Donglin Han, et al., "Preparation of chitosan/graphene oxide composite film with enhanced mechanical strength in the wet state", Carbohydrate Polymers, vol. 83, pp. 653-658 (2011).
S. Ifuku, et al., "Thermoresponsive chitosan/N-isopropylacrylamide copolymer through atom transfer radical polymerization", International Journal of Biological Macromolecules, vol. 52 pp. 14-19 (2013) Note the earliest available of this publication was Oct. 17, 2012.
Rajendra Kurapati, et al., "Near-infrared light-responsive graphene oxide composite multilayer capsules: a novel route for remote controlled drug delivery", ChemComm, vol. 49, pp. 734-736 (2013).
HN Lim, et al., "Fabrication and characterization of graphene hydrogel via hydrothermal approach as a scaffold for preliminary study of cell growth", International Journal of Nanomedicine, vol. 16, pp. 1817-1823 (2011).
Lv W., et al., "Temperature- and redox-directed multiple self assembly of poly(N-isopropylacrylamide) grafted dextran nanogels", Macromol Rapid Comm., vol. 32, pp. 1101-1107 (2011).
Jiyang Liu, et al., "MultiplepH-responsivegraphenecompositesby-non-covalent modificationwithchitosan", Talanta, vol. 101, pp. 151-156 (2012).
Prakash Rai, et al., "Development and Applications of Photo-triggered Theranostic Agents", Adv Drug Deliv Rev., vol. 62, pp. 1094-1124 (2010).
Joshua T. Robinson, et al., "Ultrasmall Reduced Graphene Oxide with High Near-Infrared Absorbance for Photothermal Therapy", Journal of the American Chemical Society, vol. 133, pp. 6825-6831 (2011).
Muhammad J.A. Shiddiky, et al., "An electrochemical immunosensor to minimize the nonspecific adsorption and to improve sensitivity of protein assays in human serum", Biosensors and Bioelectronics, vol. 38, pp. 132-137 (2012).

Spizzirri, et al., "Temperature-sensitive hydrogels by graft polymerization of chitosan and N-isopropylacrylamide for drug release", (Abstract only) Pharm Dev Technol. Dec. 27, 2011.
Lin Sun, et al., "NIR-Responsive and Lectin-Binding Doxorubicin-Loaded Nanomedicine from Janus-Type Dendritic PAMAM Amphiphiles", Biomacromoledcules, vol. 13, pp. 3581-3591, Sep. 27, 2012, e-published Oct. 9, 2012.
Brian P. Timko, et al., "Remotely Triggerable Drug Delivery Systems", Advanced Materials, vol. 22, pp. 4925-4943 (2010).
Brian P. Timko, et al., "Materials to Clinical Devices: Technologies for Remotely Triggered Drug Delivery", Clinical Therapeutics, vol. 34, pp. 11S, pp. S25-S35 (2012).
Changzheng Wu, et al., "Large-area graphene realizing ultrasensitive photothermal actuator with high transparency: new prototype robotic motions under infrared-light stimuli", Journal of Materials Chemistry, vol. 21, pp. 18584-18591 (2011).
Azami M, Moosavifar MJ, Baheiraei N, Mortarzadeh F, Ai J. Preparation of a biomimetic nanocomposite scaffold for bone tissue engineering via mineralization of gelatin hydrogel and study of mineral transformation in simulated body fluid. Journal of Biomedical Materials Research Part A. 2012;100A:1347-55.
Bahney CS, Hsu CW, Yoo JU, West JL, Johnstone B. A bioresponsive hydrogel tuned to chondrogenesis of human mesenchymal stem cells. Faseb Journal. 2011;25:1486-96.
Bhardwaj N, Kundu SC. Chondrogenic differentiation of rat MSCs on porous scaffolds of silk fibroin/chitosan blends. Biomaterials. 2012;33:2848-57.
Blakney AK, Swartzlander MD, Bryant SJ. The effects of substrate stiffness on the in vitro activation of macrophages and in vivo host response to poly(ethylene glycol)-based hydrogels. Journal of Biomedical Materials Research Part A. 2012;100A:1375-86.
Brighton CT, Krebs AG. Oxygen-Tension of Healing Fractures in Rabbit. Journal of Bone and Joint Surgery—American vol. 1972;A 54:323-&.
Callahan LAS, Ganios AM, McBurney DL, Dilisio MF, Weiner SD, Horton WE, et al. ECM Production of Primary Human and Bovine Chondrocytes in Hybrid PEG Hydrogels Containing Type I Collagen and Hyaluronic Acid. Biomacromolecules. 2012;13:1625-31.
Feng L, Zhang S, Liu Z. Graphene based gene transfection. Nanoscale. 2011;3:1252-7.
Fernandez MS, Arias JI, Martinez MJ, Saenz L, Neira-Carrillo A, Yazdani-Pedram M, et al. Evaluation of a multilayered chitosan-hydroxy-apatite porous composite enriched with fibronectin or an in vitro-generated bone-like extracellular matrix on proliferation and diferentiation of osteoblasts. Journal of Tissue Engineering and Regenerative Medicine. 2012;6:497-504.
Freier T, Koh HS, Kazazian K, Shoichet MS. Controlling cell adhesion and degradation of chitosan films by N-acetylation. Biomaterials. 2005;26:5872-8.
I. Gorelikov, L. M. Field, E. Kumacheva, 2004 Hybrid Microgels Photoresponsive in the Near-Infrared Spectral Range. Journal of the American Chemical Society, 126, 15938 0002-7863 .
Grayson, A.C.R., et al., "Multi-pulse drug delivery from a resorbable polymeric microchip device" Nature Materials (2003) 2, 767.
He XZ, Ma JY, Jabbari E. Effect of Grafting RGD and BMP-2 Protein-Derived Peptides to a Hydrogel Substrate on Osteogenic Differentiation of Marrow Stromal Cells. Langmuir. 2008;24:12508-16.
Heppenstall RB, Grislis G, Hunt TK. Tissue Gas Tensions and Oxygen-Consumption in Healing Bone Defects. Clinical Orthopaedics and Related Research. 1975:357-65.
Hoare, T., et al. "A magnetically-triggered composite membrane for on-demand drug delivery", Nano Lett.,9, 3651-57, (2009).
Hong, Y.; , et al., "Covalently crosslinked chitosan hydrogel: Properties of in vitro degradation and chondrocyte encapsulation", Acta Biomaterialia, vol. 3, Issue 1, Jan. 2007, pp. 23-31.
Huang Y, Zeng M, Ren J, Wang J, Fan L, Xu Q. Preparation and swelling properties of graphene oxide/poly(acrylic acid-co-acrylamide) super-absorbent hydrogel nanocomposites. Colloids and Surfaces a-Physicochemical and Engineering Aspects. 2012;401:97-106.

(56) References Cited

OTHER PUBLICATIONS

Kang, H.Z.& Trondoli, A.C.& Zhu, G.Z. et al., "Near-infrared light-responsive core-shell nanogels for targeted drug delivery", ACS Nano, vol. 5, 6, 2011, p. 5094-5099.

Kanichai M, Ferguson D, Prendergast PJ, Campbell VA. Hypoxia promotes chondrogenesis in rat mesenchymal stem cells: A role for AKT and hypoxia-inducible factor (HIF)-1 alpha. Journal of Cellular Physiology. 2008;216:708-15.

Khurma, J.R.& Nand, A.V., "Temperature and pH sensitive hydrogels composed of chitosan and poly(ethylene glycol)", Polymer Bulletin, vol. 59, 2008, p. 805-812.

Koay EJ, Athanasiou KA. Hypoxic chondrogenic differentiation of human embryonic stem cells enhances cartilage protein synthesis and biomechanical functionality. Osteoarthritis and Cartilage. 2008;16:1450-6.

Lee WC, Lim C, Shi H, Tang LAL, Wang Y, Lim CT, et al. Origin of Enhanced Stem Cell Growth and Differentiation on Graphene and Graphene Oxide. ACS Nano. 2011;5:7334-41.

Li WY, et al., "Gold nanocages covered with thermally-responsive polymers for controlled release by high-intensity focused ultrasound. Nanoscale", 2011;3:1724-1730. doi: 10.1039/c0nr00932f.

Lo C-W, Zhu D, Jiang H. An infrared-light responsive graphene-oxide incorporated poly(N-isopropylacrylamide) hydrogel nanocomposite. Soft Matter. 2011;7:5604-9.

Lu J, Choi E, Tamanoi F, Zink, "Light-Activated Nanoimpeller-Controlled Drug Release in Cancer Cells" Jl. Small., 2008;4:421-426.

Malladi P, Xu Y, Chiou M, Giaccia AJ, Longaker MT. Effect of reduced oxygen tension on chondrogenesis and osteogenesis in adipose-derived mesenchymal cells. American Journal of Physiology—Cell Physiology. 2006;290: C1139-C45.

Z. M. Markovic, L. M. Harhaji-Trajkovic, B. M. Todorovic-Markovic, D. P. Kepić, K. M. Arsikin, S. P. Jovanović, A. C. Pantovic, M. D. Dramićanin, and V. S. Trajkovic, "In vitro comparison of the photothermal anticancer activity of graphene nanoparticles and carbon nanotubes," Biomaterials32(4), 1121-1129 (2011).

Rana VK, Choi MC, Kong JY, Kim GY, Kim MJ, Kim SH, et al. Synthesis and Drug-Delivery Behavior of Chitosan-Functionalized Graphene Oxide Hybrid Nanosheets. Macromolecular Materials and Engineering. 2011;296:131-40.

Motoi Oishi, et al., "Endosomal release and intracellular delivery of anticancer drugs using pH-sensitive PEGylated nanogels", J. Mater. Chem., 2007,17, 3720-3725.

Panyukhin NV, Vishnyakova KS, Yegorov YE. Influence of Partial Oxygen Pressure on Survival, Proliferation, and Differentiation of Mesenchymal Stem Cells from Mouse Bone Marrow. Biologicheskie Membrany. 2008;25:352-9.

Potier E, Ferreira E, Andriamanalijaona R, Pujol J-P, Oudina K, Logeart-Avramoglou D, et al. Hypoxia affects mesenchymal stromal cell osteogenic differentiation and angiogenic factor expression. Bone. 2007;40:1078-87.

Roostaeian J, Carlsen B, Simhaee D, Jarrahy R, Huang WB, Ishida K, et al. Characterization of growth and osteogenic differentiation of rabbit bone marrow stromal cells. Journal of Surgical Research. 2006;133:76-83.

Sahu, A. et al., "A Stimuli-Sensitive Injectable Graphene Oxide Composite Hydrogel", Chemical Communications (2012) 48, 5820-5822.

Santini, J. T. et al., "A controlled-Release Microship", Nature (1999) 397, 335-338.

S. R. Sershen, et al., "2000 Temperature-sensitive polymer-nanoshell composites for photothermally modulated drug delivery". Journal of Biomedical Materials Research, 51, 293 0021-9304.

S. R. Sershen, et al, "2001 an opto-mechanical nanoshell-polymer composite." Applied Physics B: Lasers and Optics, 73, 379 0946-2171.

Sherlock, S. P. et al., "Photothermally Enhanced Drug Delivery by Ultra-Small Multifunctional FeCo/Graphitic-Shell Nanocrystals", ACS Nano (2011) 5, 1505-1512.

Shi, F.H.& Ding, J.X.& Xiao, C.S. et al., "Intracellular microenvironment responsive PEGylated polypeptide nanogels with ionizable cores for efficient doxorubicin loading and triggered release", J Mater Chem, vol. 22, 28, 2012, p. 14168-14179.

Shiotani A, et al., "Stable incorporation of gold nanorods into N-isopropylacrylamide hydrogels and their rapid shrinkage induced by near-infrared laser irradiation." Langmuir. 2007;23:4012-8.

Stankovich S, Dikin DA, Dommett GHB, Kohlhaas KM, Zimney EJ, Stach EA, et al. Graphene-based composite materials. Nature. 2006;442:282-6.

Sun X, Liu Z, Welsher K, Robinson JT, Goodwin A, Zaric S, et al. Nano-Graphene Oxide for Cellular Imaging and Drug Delivery. Nano Research. 2008;1:203-12.

Tanuma H, Kiuchi H, Kai WH, Yazawa K, Inoue Y. Characterization and Enzymatic Degradation of PEG-Cross-Linked Chitosan Hydrogel Films. Journal of Applied Polymer Science. 2009;114:1902-7.

Tian B, Wang C, Zhang S, Feng L, Liu Z. Photothermally enhanced photodynamic therapy delivered by nano-graphene oxide. ACS Nano. 2011;5:7000-9.

Thomas, C. R. et al., "Noninvasive remote-controlled release of drug molecules in vitro using magnetic actuation of mechanized nanoparticles.", J. of the American Chemical Society (2010) 132, 10623.

C. Wang, et al., "Controlled structure and properties of thermoresponsive nanoparticle-hydrogel composites," Advanced Materials, vol. 16, No. 13, pp. 1074-1079, 2004.

Wang C, Yu B, Knudsen B, Harmon J, Moussy F, Moussy Y. Synthesis and performance of novel hydrogels coatings for implantable glucose sensors. Biomacromolecules. 2008;9:561-7.

Wu G, , et al., "Remotely Triggered Liposome Release by Near-Infrared Light Absorption via Hollow Gold Nanoshells." Journal of the American Chemical Society. 2008;130:8175-8177.

Yang, K. et al., "Graphene in mice: ultrahigh in vivo tumor uptake and efficient photothermal therapy." Nano Letters (2010) 10, 3318.

Yang K, et al., "In vivo pharmacokinetics, long-term biodistribution, and toxicology of PEGylated graphene in mice." ACS Nano. 2011;5:516-22.

Yang K. et al. Multimodal imaging guided photothermal therapy using functionalized graphene nanosheets anchored with magnetic nanoparticles. Adv. Mater. 24, 1868-1872.

Yang XY, et al. Multi-functionalized graphene oxide based anticancer drug-carrier with dual-targeting function and pH-sensitivity. J Mater Chem. 2011;21(10):3448-3454.

Yavuz, M. S. et al., "Gold nanocages covered by smart polymers for controlled release with near-infrared light." Nature Materials (2009) 8, 935.

Yoshida H, Hatakeyama T, Hatakeyama H. Characterization of Water in Polysaccharide Hydrogels by DSC. Journal of Thermal Analysis. 1993;40:483-9.

Zakhem E, Raghavan S, Gilmont RR, Bitar KN. Chitosan-based scaffolds for the support of smooth muscle constructs in intestinal tissue issue engineering. Biomaterials. 2012;33:4810-7.

Zhang LM, Xia JG, Zhao QH, Liu LW, Zhang ZJ. Functional Graphene Oxide as a Nanocarrier for Controlled Loading and Targeted Delivery of Mixed Anticancer Drugs. Small. 2010;6:537-44.

Zhang L, Wang Z, Xu C, Li Y, Gao J, Wang W, et al. High strength graphene oxide/polyvinyl alcohol composite hydrogels. Journal of Materials Chemistry. 2011;21:10399-406.

Miura M, Miura Y, Sonoyama W, Yamaza T, Gronthos S, Shi S. Bone marrow-derived mesenchymal stem cells for regenerative medicine in craniofacial region. Oral Diseases. 2006;12:514-22.

Slaughter BV, Khurshid SS, Fisher OZ, Khademhosseini A, Peppas NA. Hydrogels in Regenerative Medicine. Advanced Materials. 2009;21:3307-29.

Cong H-P, Ren X-C, Wang P, Yu S-H. Macroscopic Multifunctional Graphene-Based Hydrogels and Aerogels by a Metal Ion Induced Self-Assembly Process. Acs Nano. 2012;6:2693-703.

Guo ZY, Hao TT, Duan J, Wang S, Wei DY. Electrochemiluminescence immunosensor based on graphene-CdS quantum dots-agarose composite for the ultrasensitive detection of alpha fetoprotein. Talanta. 2012;89:27-32.

(56) References Cited

OTHER PUBLICATIONS

Hou CY, Zhang QH, Li YG, Wang HZ. P25-graphene hydrogels: Room-temperature synthesis and application for removal of methylene blue from aqueous solution. Journal of Hazardous Materials. 2012;205:229-35.

Bai H, Li C, Wang X, Shi G. A pH-sensitive graphene oxide composite hydrogel. Chemical Communications. 2010;46:2376-8.

Adhikari B, Biswas A, Banerjee A. Graphene Oxide-Based Supramolecular Hydrogels for Making Nanohybrid Systems with Au Nanoparticles. Langmuir. 2012;28:1460-9.

Yang X, Qiu L, Cheng C, Wu Y, Ma Z-F, Li D. Ordered Gelation of Chemically Converted Graphene for Next-Generation Electroconductive Hydrogel Films. Angewandte Chemie—International Edition. 2011;50:7325-8.

Zhang XT, Sui ZY, Xu B, Yue SF, Luo YJ, Zhan WC, et al. Mechanically strong and highly conductive graphene aerogel and its use as electrodes for electrochemical power sources. Journal of Materials Chemistry. 2011;21:6494-7.

Zhang N, Li R, Zhang L, Chen H, Wang W, Liu Y, et al. Actuator materials based on graphene oxide/polyacrylamide composite hydrogels prepared by in situ polymerization. Soft Matter. 2011;7:7231-9.

Lim HN, Huang NM, Lim SS, Harrison I, Chia CH. Fabrication and characterization of graphene hydrogel via hydrothermal approach as a scaffold for preliminary study of cell growth. International Journal of Nanomedicine. 2011;6:1817-23.

Sun S, Wu P. A one-step strategy for thermal- and pH-responsive graphene oxide interpenetrating polymer hydrogel networks. Journal of Materials Chemistry. 2011;21:4095-7.

Kalbacova M, Broz A, Kong J, Kalbac M. Graphene substrates promote adherence of human osteoblasts and mesenchymal stromal cells. Carbon. 2010;48:4323-9.

Nayak TR, Andersen H, Makam VS, Khaw C, Bae S, Xu XF, et al. Graphene for Controlled and Accelerated Osteogenic Differentiation of Human Mesenchymal Stem Cells. Acs Nano. 2011;5:4670-8.

Woods A, Khan S, Beier F. C-type natriuretic peptide regulates cellular condensation and glycosaminoglycan synthesis during chondrogenesis. Endocrinology. 2007;148:5030-41.

Tataria M, Quarto N, Longaker MT, Sylvester KG. Absence of the p53 tumor suppressor gene promotes osteogenesis in mesenchymal stem cells. Journal of Pediatric Surgery. 2006;41:624-32.

Khurma JR, Nand AV. Temperature and pH sensitive hydrogels composed of chitosan and poly(ethylene glycol). Polymer Bulletin. 2008;59:805-12.

Hong Y, Song HQ, Gong YH, Mao ZW, Gao CY, Shen JC. Covalently crosslinked chitosan hydrogel: Properties of in vitro degradation and chondrocyte encapsulation. Acta Biomaterialia. 2007;3:23-31.

Hong L, Peptan I, Clark P, Mao JJ. Ex vivo adipose tissue engineering by human marrow stromal cell seeded gelatin sponge. Annals of Biomedical Engineering. 2005;33:511-7.

Gomillion CT, Burg KJL. Stem cells and adipose tissue engineering. Biomaterials. 2006;27:6052-63.

Patrick CW. Adipose tissue engineering: The future of breast and soft tissue reconstruction following tumor resection. Seminars in Surgical Oncology. 2000;19:302-11.

Morgan SM, Ainsworth BJ, Kanczler JM, Babister JC, Chaudhuri JB, Oreffo ROC. Formation of a human-derived fat tissue layer in P(DL)LGA hollow fibre scaffolds for adipocyte tissue engineering. Biomaterials. 2009;30:1910-7.

Alhadlaq A, Tang M, Mao JJ. Engineered adipose tissue from human mesenchymal stem cells maintains predefined shape and dimension: Implications in soft tissue augmentation and reconstruction. Tissue Engineering. 2005; 11:556-66.

Valorani MG, Montelatici E, Germani A, Biddle A, D'Alessandro D, Strollo R, et al. Pre-culturing human adipose tissue mesenchymal stem cells under hypoxia increases their adipogenic and osteogenic differentiation potentials. Cell Proliferation. 2012;45:225-38.

Suga H, Eto H, Aoi N, Kato H, Araki J, Doi K, et al. Adipose Tissue Remodeling under Ischemia: Death of Adipocytes and Activation of Stem/Progenitor Cells. Plastic and Reconstructive Surgery. 2010;126:1911-23.

Pittenger MF, Mackay AM, Beck SC, Jaiswal RK, Douglas R, Mosca JD, et al. Multilineage potential of adult human mesenchymal stem cells. Science. 1999;284:143-7.

Tsai MT, Li WJ, Tuan RS, Chang WH. Modulation of Osteogenesis in Human Mesenchymal Stem Cells by Specific Pulsed Electromagnetic Field Stimulation. Journal of Orthopaedic Research. 2009;27:1169-74.

Fehrer C, Brunauer R, Laschober G, Unterluggauer H, Reitinger S, Kloss F, et al. Reduced oxygen tension attenuates differentiation capacity of human mesenchymal stem cells and prolongs their lifespan. Aging Cell. 2007;6:745-57.

* cited by examiner

GRAPHENE HYDROGEL AND METHOD FOR USING THE SAME

CROSS REFERENCE TO RELATED APPLICATIONS

This application claims the priority benefit of U.S. Provisional Patent Application Ser. No. 61/602,352 filed on Feb. 23, 2012, and U.S. Provisional Patent Application Ser. No. 61/602,378 filed on Feb. 23, 2012.

STATEMENT REGARDING FEDERALLY SPONSORED RESEARCH OR DEVELOPMENT

This invention was made with Government support under 1R41CA139785 and 5R01CA152005 grants awarded by the National Institutes of Health. The U.S. Government has certain rights in this invention.

BACKGROUND OF THE INVENTION

1) Field of the Invention

The present invention relates to the field of hydrogels and methods for their use.

2) Description of Related Art

A hydrogel is a network of polymer chains that are hydrophilic, sometimes found as a colloidal gel in which water is the dispersion medium. Hydrogels are highly absorbent (they can contain over 99.9% water) natural or synthetic polymers. Hydrogels also possess a degree of flexibility very similar to natural tissue due to their significant water content.

Hydrogels are used in a multitude of applications. Hydrogels are used in products as diverse as disposable diapers, contact lenses, EEG and ECG medical electrodes, and water gel explosives. Hydrogels are also used in many biotechnology-related applications. For example, hydrogels are used as scaffolds in tissue engineering and hydrogel-coated wells have been used for cell culture. Environmentally sensitive hydrogels have been created that have the ability to sense changes of pH, temperature, or the concentration of a metabolite and release their load as result of such changes. Hydrogels have also been created for sustained-release drug delivery systems. Some hydrogels are responsive to specific molecules, such as glucose or antigens, and can be used as biosensors.

Noninvasive externally-controlled hydrogel drug release systems are attractive since they allow remote, repeatable and reliable switching on or off of drug release based on need. Generally, a noninvasive remote-controlled drug delivery system comprises a drug, an external stimulus, stimulus-sensitive materials, and stimulus-responsive carriers. The external stimulus can be light, a magnetic field, or ultrasound or radio-frequency [Yavuz, M. S. et al., Nature Materials (2009) 8, 935; Sherlock, S. P. et al., Acs Nano (2011) 5, 1505; Lu, J. et al., Small (2008) 4, 421; Hoare, T. et al., Nano Letters (2009) 9, 3651; Thomas, C. R. et al., J. of the American Chemical Society (2010) 132, 10623; Li, W. Y. et al., Nanoscale (2011) 3, 1724; Santini, J. T. et al., Nature (1999) 397, 335; Grayson, A. C. R. et al., Nature Materials (2003) 2, 767].

An NIR light-triggered release system utilizes the photothermal property of a material, which absorbs NIR light and converts it into heat, thereby inducing the drug release from a thermosensitive carrier. Photothermal materials with strong optical absorbance in the NIR include various gold nanostructures (gold nanorods, gold nanocages, hollow gold nanospheres, gold nanoshells), carbon materials (carbon nanotubes, graphene), or conducting polymers that have been extensively studied for photothermal therapy [Markovic, Z. M. et al., Biomaterials (2011) 32, 1121; Yang, K. et al., Nano Letters (2010) 10, 3318; Tian, B. et al., Acs Nano (2011) 5, 7000; Yang, K. et al., Advanced Materials (2012) 24, 1868]. Gold nanoparticles, gold nanorods, and gold nanocages have been studied for the NIR-triggered drug release by incorporation into thermo-responsive materials [Yavuz, M. S. et al., Nature Materials (2009) 8, 935; Li, W. Y. et al., Nanoscale (2011) 3, 1724; Wu, G. H. et al., J. of the American Chemical Society (2008) 130, 8175]. However, none of these delivery systems have been advanced to clinical trials yet.

Two-dimensional graphene has received considerable attention in biomedical applications in the past few years owing to its high mechanical strength, pH sensitivity, photosensitivity and low toxicity [Yang, K. et al., Nano Letters (2010) 10, 3318; Yang, K. et al., Acs Nano (2011) 5, 516; Yang, X. Y. et al., J. of Materials Chemistry (2011) 21, 3448]. Graphene shows higher photothermal sensitivity than carbon nanotubes (CNT) and was shown to be highly effective in photothermal therapy for cancer [Markovic, Z. M. et al., Biomaterials (2011) 32, 1121; Yang, K. et al., Nano Letters (2010) 10, 3318; Tian, B. et al., Acs Nano (2011) 5, 7000; Yang, K. et al., Advanced Materials (2012) 24, 1868]. In addition, the highly efficient photothermal conversion of graphene enabled graphene oxide/pluronic hydrogel to undergo rapid gelation by NIR laser irradiation [Lo, C.-W. et al., Soft Matter (2011) 7, 5604; Sahu, A. et al., Chemical Communications (2012) 48, 5820]. Whether chemically reduced graphene oxide (GRAPHENE) is capable of acting as a photosensitive material for remote-controlled drug delivery has not been investigated yet.

As mentioned above, hydrogels have also been found to be advantageous when used as scaffolds for cell growth and, in particular, for tissue regeneration. Researchers have found that poor results are obtained when growing cells in a monolayer due to the vast differences in the monolayer cell environment and the in vivo cell environment. Cell morphology, extracellular matrix interactions, three-dimensional organization, oxygen tension, and access to extracellular factors all differ greatly between cells found in a monolayer and cells found in vivo.

Recently, three-dimensional cell cultures have emerged as an alternative to a flat layer of cells. Three-dimensional cell cultures are cellular networks organized in three dimensions—an environment that is much more similar to that found in vivo. Three-dimensional cell cultures have been created using tumor spheroids, embryoid bodies, hanging drop cell cultures, fibrous networks and hydrogels.

Hydrogels are an attractive scaffolding material because their mechanical properties can be tailored to mimic those of natural tissues. As scaffolds, hydrogels are used to provide bulk and mechanical constitution to a tissue construct, whether cells are adhered to or suspended within the three dimensional gel framework. When cellular adhesion directly to the gel is favored over suspension within the scaffold, incorporation of various peptide domains into the hydrogel structure can dramatically increase the tendency for cellular attachment. A particularly successful strategy to mediate cellular attachment is the inclusion of the RGD adhesion peptide sequence (arginine-glycine-aspartic acid). Cells that have been shown to favorably bind to RGD include fibroblasts, endothelial cells (ECs), smooth muscle cells (SMCs), osteoblasts, and chondrocytes. RGD in hydrogels, which can be incorporated on the surface or throughout the bulk of the gel, has shown enhanced cellular migration, proliferation, growth, and organization in tissue regeneration applications.

DETAILED DESCRIPTION OF THE INVENTION

Figure 1A:
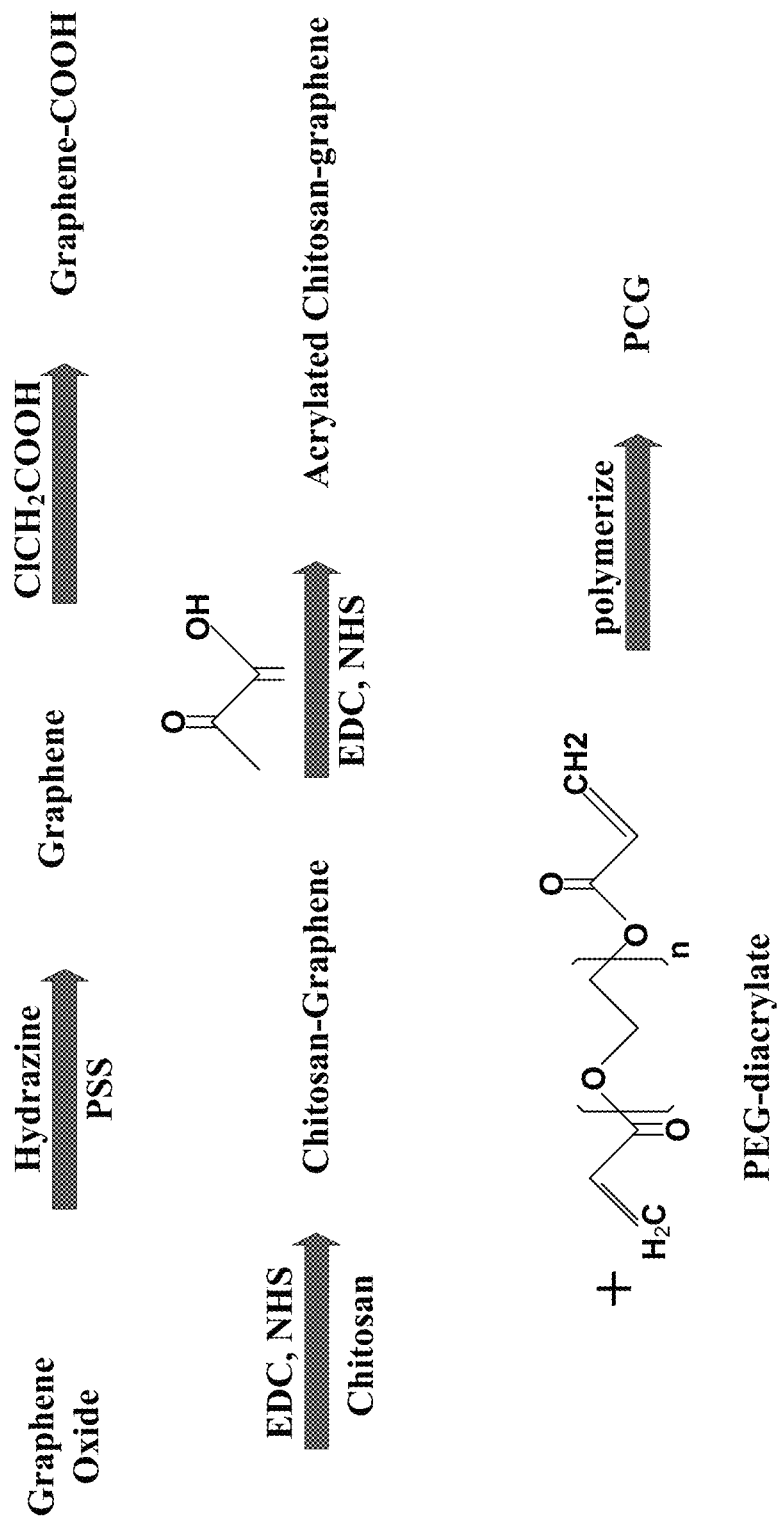
FIG. 1 (A-E) is a schematic of PCG hydrogel synthesis.
Figure 1B:
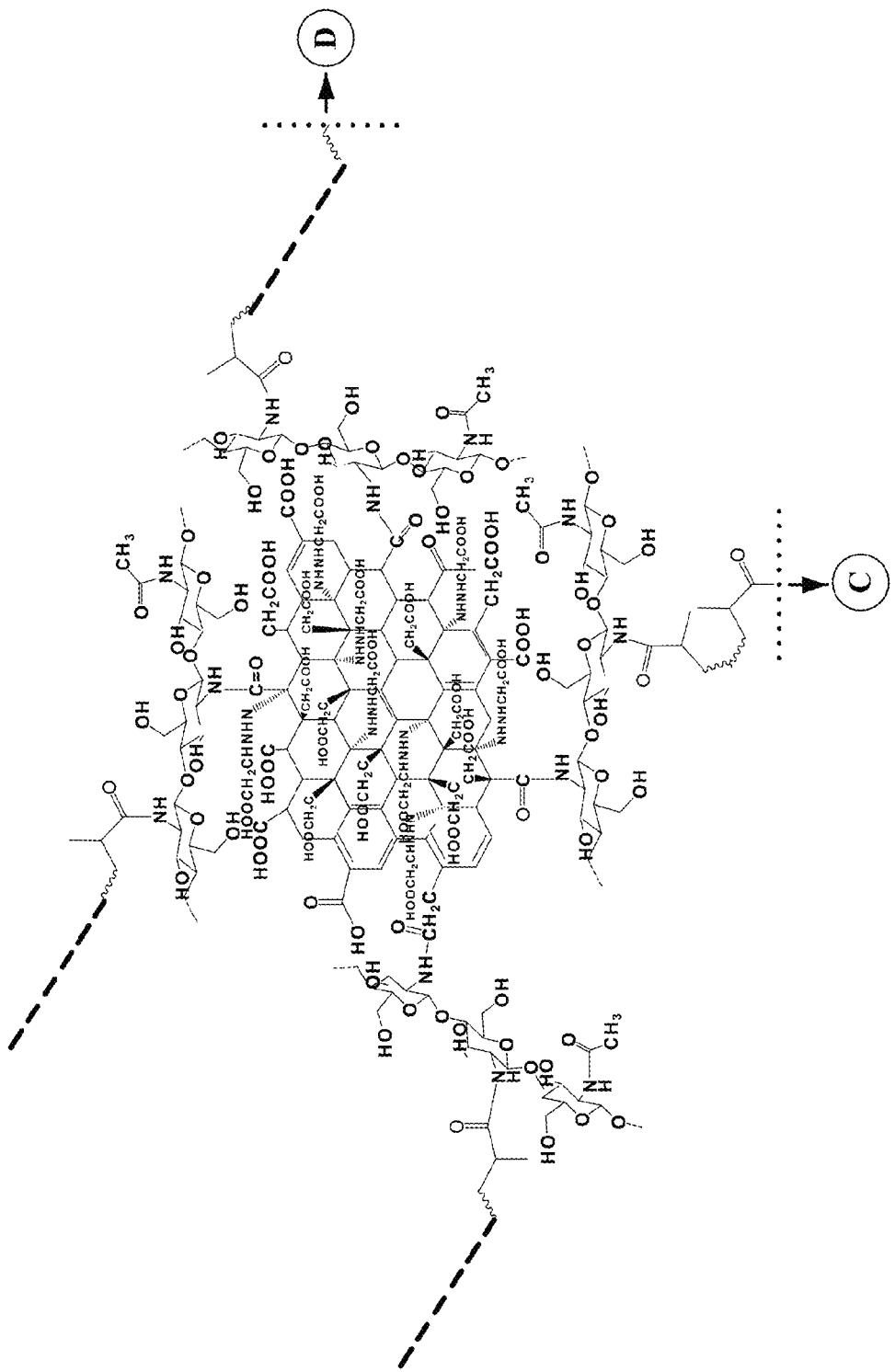
Figure 1C:
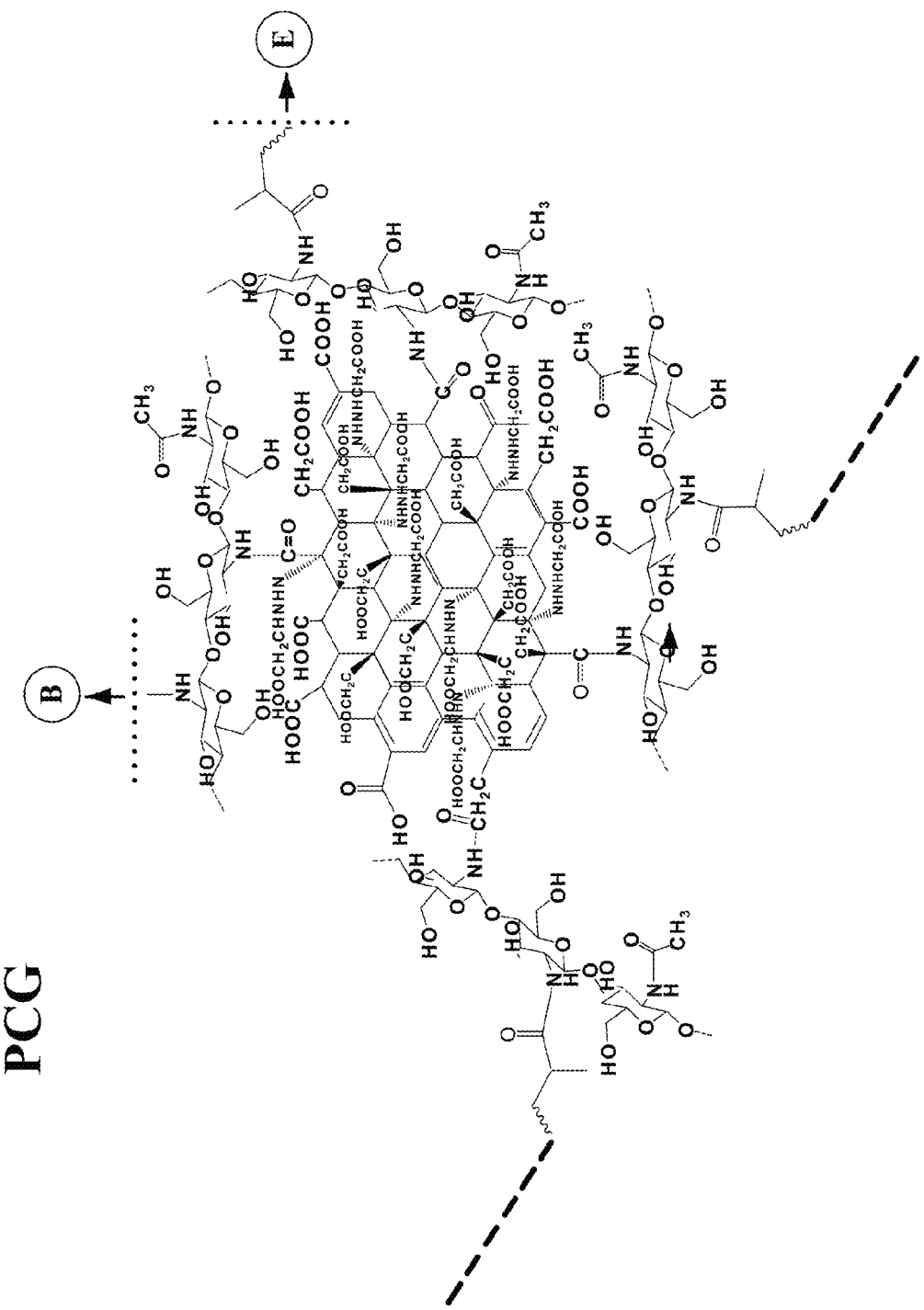
Figure 1D:
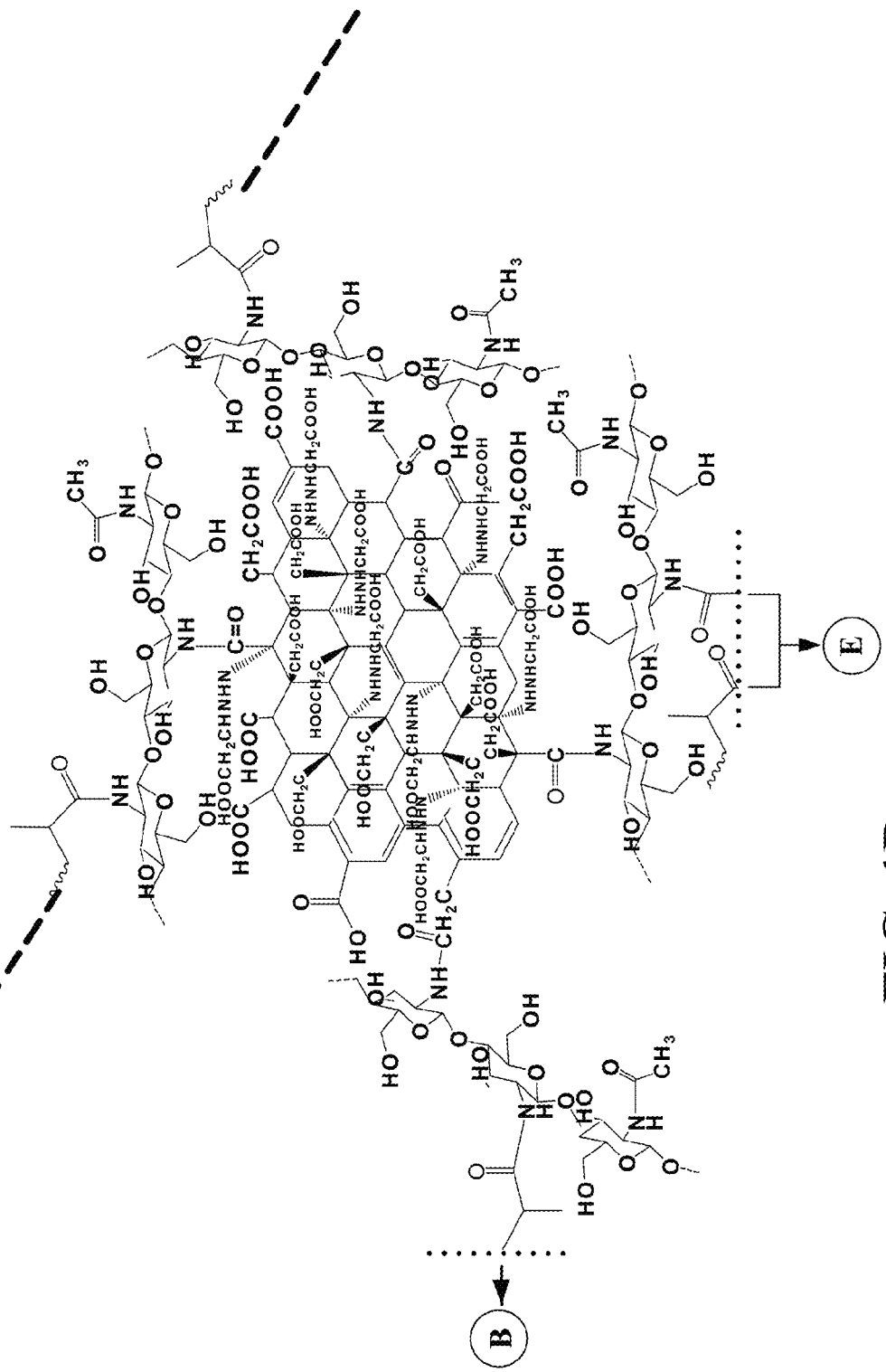
Figure 1E:
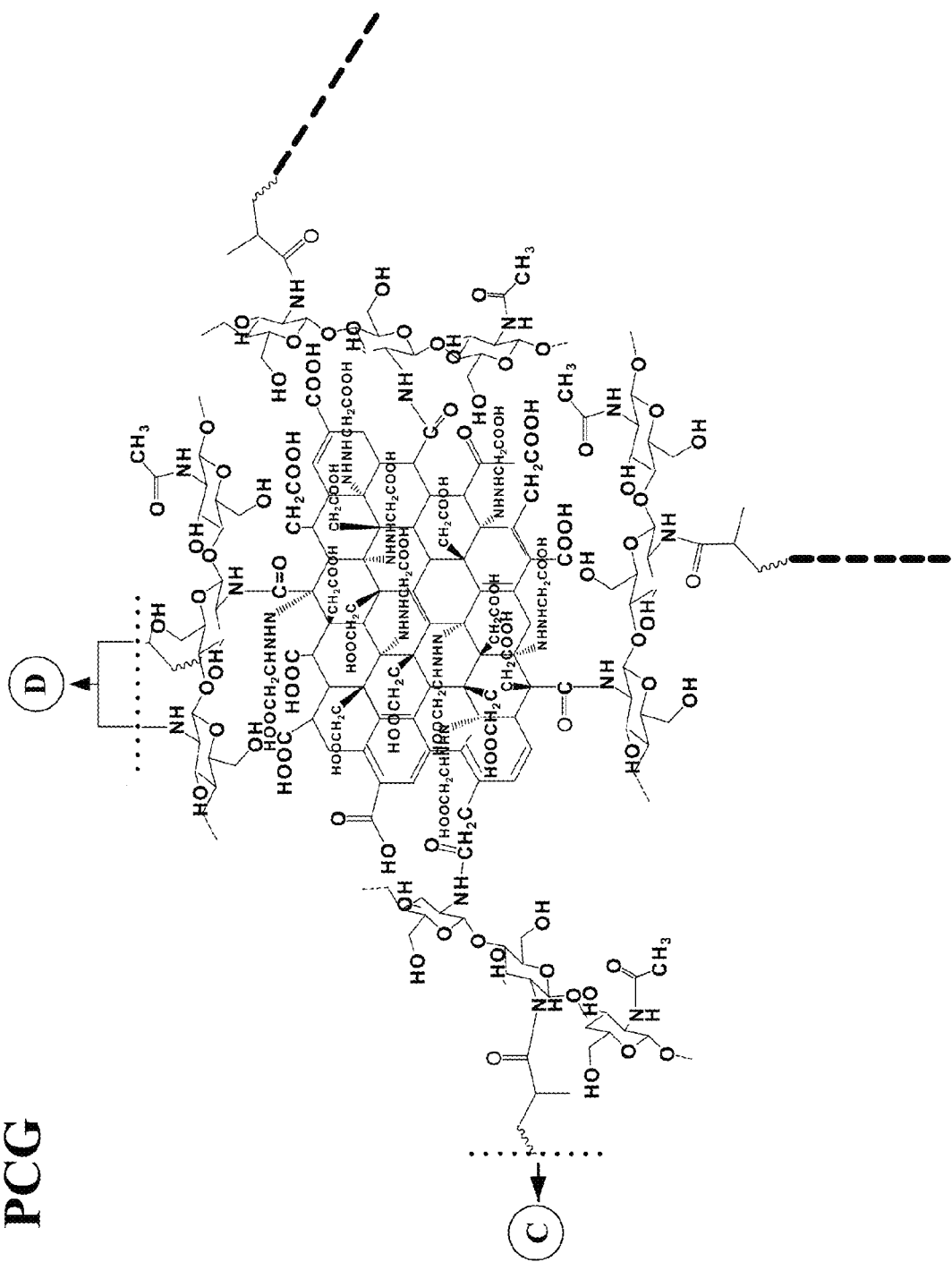

Provided herein is a hydrogel composition comprising a graphene, a chitosan, and a polyethylene (glycol) diacrylate (PEGDA). The term "PCG hydrogel" is used herein to describe the PEGDA-chitosan-graphene hydrogel. Also provided herein is a hydrogel composition comprising a graphene, a chitosan, a PEGDA, and an N-isopropylacrylamide (NIPAM). The term "TPCG" is used to describe the NIPAM-PEGDA-chitosan-graphene hydrogel. It is a surprising finding of the present invention that a PCG hydrogel supports the differentiation of mesenchymal stem cells into adipocytes, chondrocytes and osteocytes. Accordingly, also provided is a method for differentiating a mesenchymal stem cell comprising contacting the cell with the PCG hydrogel. It is also a surprising finding of the present invention that a TPCG hydrogel can serve as a thermally inducible delivery vehicle for a pharmaceutical composition. Accordingly, further provided herein is a method for delivering a pharmaceutical composition to a cell comprising administering to the cell a TPCG hydrogel and the pharmaceutical composition.

Term definitions used in the specification and claims to describe the present invention are as follows.

Definitions

As used in the specification and claims, the singular form "a," "an," and "the" include plural references unless the context clearly dictates otherwise. For example, the term "a cell" includes a plurality of cells, including mixtures thereof.

The term "adipocyte" refers to a cell type also known as a lipocyte or fat cell. Adipocytes are the cells that primarily compose adipose tissue, specialized in storing energy as fat.

The term "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

As used herein, the terms "cancer," "cancer cells," "neoplastic cells," "neoplasia," "tumor," and "tumor cells" (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign. A metastatic cell or tissue means that the cell can invade and destroy neighboring body structures. The cancer can be selected from astrocytoma, adrenocortical carcinoma, appendix cancer, basal cell carcinoma, bile duct cancer, bladder cancer, bone cancer, brain cancer, brain stem glioma, breast cancer, cervical cancer, colon cancer, colorectal cancer, cutaneous T-cell lymphoma, ductal cancer, endometrial cancer, ependymoma, Ewing sarcoma, esophageal cancer, eye cancer, gallbladder cancer, gastric cancer, gastrointestinal cancer, germ cell tumor, glioma, hepatocellular cancer, histiocytosis, Hodgkin lymphoma, hypopharyngeal cancer, intraocular melanoma, Kaposi sarcoma, kidney cancer, laryngeal cancer, leukemia, liver cancer, lung cancer, lymphoma, macroglobulinemia, melanoma, mesothelioma, mouth cancer, multiple myeloma, nasopharyngeal cancer, neuroblastoma, non-Hodgkin lymphoma, osteosarcoma, ovarian cancer, pancreatic cancer, parathyroid cancer, penile cancer, pharyngeal cancer, pituitary cancer, prostate cancer, rectal cancer, renal cell cancer, retinoblastoma, rhabdomyosarcoma, sarcoma, skin cancer, small cell lung cancer, small intestine cancer, squamous cell carcinoma, stomach cancer, T-cell lymphoma, testicular cancer, throat cancer, thymoma, thyroid cancer, trophoblastic tumor, urethral cancer, uterine cancer, uterine sarcoma, vaginal cancer, vulvar cancer and Wilms tumor.

The terms "cell," "cell line," and "cell culture" include progeny. It is also understood that all progeny may not be precisely identical in DNA content, due to deliberate or inadvertent mutations. Variant progeny that have the same function or biological property, as screened for in the originally transformed cell, are included. The "host cells" used in the present invention generally are prokaryotic or eukaryotic hosts.

The term "chondrocyte" refers to a differentiated cell or chondrocyte progenitor cell normally found in healthy cartilage. Chondrocytes produce and maintain the cartilaginous matrix, which consists mainly of collagen and proteoglycans.

A "composition" is intended to mean a combination of active agent and another compound or composition, inert (for example, a detectable agent or label) or active, such as an adjuvant.

As used herein, the term "comprising" is intended to mean that the compositions and methods include the recited elements, but not excluding others. "Consisting essentially of," when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purpose. A control can be "positive" or "negative."

The term "differentiation" refers herein to the process by which a less specialized cell becomes a more specialized cell type.

An "effective amount" is an amount sufficient to effect beneficial or desired results. An effective amount can be administered in one or more administrations, applications or dosages.

The term "isolated" means separated from constituents, cellular and otherwise, in which the polynucleotide, peptide, polypeptide, protein, antibody, or fragments thereof are normally associated with in nature. In one aspect of this invention, an isolated polynucleotide is separated from the 3' and 5' contiguous nucleotides with which it is normally associated with in its native or natural environment, e.g., on the chromosome. As is apparent to those of skill in the art, a non-naturally occurring polynucleotide, peptide, polypeptide, protein, or antibody, or fragments thereof, does not require "isolation" to distinguish it from its naturally occurring counterpart. In addition, a "concentrated," "separated," or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, or antibody, or fragments thereof, which differs from the naturally occurring counterpart in its primary sequence or, for example, by its glycosylation pattern, need not be present in its isolated form since it is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature.

"Mammal" for purposes of treatment refers to any animal classified as a mammal, including human, domestic and farm animals, nonhuman primates, and zoo, sports, or pet animals, such as dogs, horses, cats, cows, etc.

The term "mesenchymal stem cell," or "MSC," refers to a multipotent stromal cell that can differentiate into a variety of cell types including osteoblasts, chondrocytes, and adipocytes. A cell can be classified as an MSC if it shows plastic adherent properties under normal culture conditions and has a fibroblast-like morphology. In some embodiments, an MSC expresses on the surface CD73, CD90 and CD105, while lacking the expression of CD11b, CD14, CD19, CD34, CD45, CD79a and HLA-DR surface markers.

A "mesenchymal stem cell product" refers to a differentiated cell such as an osteoblast, chondrocyte, or adipocyte or a composition produced by an osteoblast, chondrocyte, or adipocyte.

The term "osteoblast" refers to a differentiated cell or osteoblast progenitor cell that is normally located in the deeper layer of periosteum and the bone marrow that generates bone tissue. In some embodiments, an osteoblast expresses a range of genetic markers including Osterix, Col1, BSP, M-CSF, ALP, osteocalcin, osteopontin, and osteonectin.

The term "osteocyte" refers to a star shaped cell that is most commonly found in mature bone. Osteocytes are cells that contain a nucleus and a thin ring piece of cytoplasm. When osteoblasts become trapped in the matrix that they secrete, they become osteocytes.

The term "particulate" refers to powders, granular substances, and the like.

A "pharmaceutical composition" is intended to include the combination of an active agent with a carrier, inert or active, making the composition suitable for diagnostic or therapeutic use in vitro, in vivo, or ex vivo.

As used herein, the term "pharmaceutically acceptable carrier" encompasses any of the standard pharmaceutical carriers, such as a phosphate buffered saline solution, water, emulsions, such as an oil/water or water/oil emulsion, and various types of wetting agents. The compositions also can include stabilizers and preservatives. For examples of carriers, stabilizers, and adjuvants, see Martin, REMINGTON'S PHARM. SCI., 15th Ed. (Mack Publ. Co., Easton (1975)).

The term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The term "pharmaceutically acceptable salts" refers to any acid or base addition salt whose counter-ions are non-toxic to the subject to which they are administered in pharmaceutical doses of the salts. Specific examples of pharmaceutically acceptable salts are provided below.

The terms "pharmaceutically effective amount," "therapeutically effective amoun," or "therapeutically effective dose" refer to the amount of a compound such as a mesenchymal stem cell product that will elicit the biological or medical response of a tissue, system, animal, or human that is being sought by the researcher, veterinarian, medical doctor or other clinician. The terms "prevent," "preventing," "prevention," and grammatical variations thereof as used herein refer to a method of partially or completely delaying or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms.

A "subject," "individual," or "patient," used interchangeably herein, refers to a vertebrate, preferably a mammal, more preferably a human. Mammals include, but are not limited to, murines, simians, humans, farm animals, sport animals, and pets.

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool.

The terms "pharmaceutically effective amount," "therapeutically effective amount," or "therapeutically effective dose" refer to the amount of a compound such as a mesenchymal stem cell product that will elicit the biological or medical response of a tissue, system, animal, or human that is being sought by the researcher, veterinarian, medical doctor or other clinician.

The term "therapeutically effective amount" includes that amount of a compound such as a mesenchymal stem cell product that, when administered, is sufficient to prevent development of, or alleviate to some extent, one or more of the symptoms of the condition or disorder being treated. The therapeutically effective amount will vary depending on the compound such as a mesenchymal stem cell product, the disorder or conditions and their severity, the route of administration, time of administration, rate of excretion, drug combination, judgment of the treating physician, dosage form, and the age, weight, general health, sex and/or diet of the subject to be treated. In the context of the present method, a pharmaceutically or therapeutically effective amount or dose of a mesenchymal stem cell product includes an amount that is sufficient to increase healing of a bone fracture or tissue regeneration.

The terms "treat," "treating," "treatment," and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially.

Using these terms and definitions, provided herein is a hydrogel composition comprising a graphene, a chitosan, and a polyethylene (glycol) diacrylate (PEGDA). PEGDA was chosen as the cross linker since it has been studied extensively in many biomedical applications due to its outstanding physico-chemical and biological properties such as hydrophilicity, biocompatibility, and lack of toxicity [Khurma, J. R. & Nand, A. V. Polymer Bulletin (2008) 59, 805; Blakney, A. K. et al., J. of Biomedical Materials Research Part A (2012) 100A, 1375; Callahan, L. A. S. et al., Biomacromolecules (2012) 13, 1625]. Chitosan is a linear polysaccharide prepared by partially or fully deacetylating chitin and is the second most abundant natural polymer found in the shells of shrimps, lobsters and crabs [Zakhem, E. et al., Biomaterials (2012) 33, 4810]. Due to its biocompatibility, biodegradability, and unique physicochemical properties, chitosan has been widely studied in biomedical applications [Azami, M. et al., J. of Biomedical Materials Research Part A (2012) 100A, 1347; Fernandez, M. S. et al., J. of Tissue Engineering and Regenerative Medicine (2012) 6, 497]. The 2D graphene sheet is a new biocompatible material that has been studied in the areas of controlled drug delivery, gene delivery, cell culture, cell imaging, and biosensors [Lee, W. C. et al., Acs Nano (2011) 5, 7334; Sun, X. et al., Nano Research (2008) 1, 203; Rana, V. K. et al., Macromolecular Materials and Engineering (2011) 296, 131; Bao, H. Q. et al., Small, (2011) 7, 1569; Zhang, L. M. et al., Small, (2010) 6, 537; Feng, L. et al., Nanoscale, (2011) 3, 1252].

In one embodiment, the PEGDA has a molecular weight of approximately 3400 Da. The PEDGA can also have a molecular weight of approximately 250 Da, 575 Da, 700 Da, 2,000 Da, or 6,000 Da. In another or further embodiment, the PEGDA comprises approximately 95% acrylation. In other or further embodiments, the chitosan has a molecular weight of approximately 10 kDa. The chitosan can also have a molecular weight of approximately 5 kDa, 15 kDa, 20 kDa or 30 kDa. The chitosan can be water soluble or water insoluble, and in one embodiment, the chitosan is water soluble and approximately 10 kDa in molecular weight.

The graphene used in the PCG hydrogel can be any graphene that can be covalently bonded to chitosan and PEGDA. In some embodiments, the graphene is functionalized with an oxygenous group such as hydroxyl, epoxide, or carboxyl. In one embodiment, the graphene is a carboxylic acid functionalized graphene. The carboxylic acid functionalized graphene can be prepared using graphene oxide at a concentration of approximately 0.25 mg/ml, 0.5 mg/ml, 1 mg/ml, 2 mg/ml, or 3 mg/ml. In some embodiments, the PCG hydrogel is prepared by covalent bonding of chitosan to a carboxylic acid functionalized graphene to form a chitosan-graphene composition. The chitosan-graphene composition is then acrylated and a PEGDA is covalently bonded to the acrylated chitosan-graphene.

Conventionally, nanoparticles such as graphene were embedded in gels by polymerization of a mixture of the monomer and nanoparticles [Sershen, S. R. et al., J. of Biomedical Materials Research (2000) 51, 293; Sershen, S. R. et al., Applied Physics B-Lasers and Optics (2001) 73, 379; Wang, C. et al., Advanced Materials (2004) 16, 1074]. However, the physical dispersion of nanoparticles inside the gels was not stable and uniform [Shiotani, A. et al., Langmuir (2007) 23, 4012]. The present invention provides a means for stable incorporation of graphene into a gel. More specifically, graphene was grafted with positively charged hydrophilic chitosan, which can increase the dissolution of nanoparticles and prevent the aggregation [Bao, H. Q. et al., Small (2011) 7, 1569]. Compared to conventional physical mixing, the graphene nanoparticles were uniformly dispersed inside the nanogel via chemical bonds. The PCG nanogels maintained their dispersion stability and exhibited no aggregation or precipitation for three to four months.

It is a surprising finding of the present invention that a PCG hydrogel supports the differentiation of mesenchymal stem cells into adipocytes, chondrocytes, and osteoblasts. Accordingly, also provided herein is a method of differentiating a mesenchymal stem cell comprising contacting the cell with a PCG hydrogel composition. Differentiated mesenchymal stem cells include adipocytes, chondrocytes, osteoblasts and osteoclasts, and their post-MSC progenitors. Further provided herein is a PCG hydrogel composition further comprising a mesenchymal stem cell, a wholly or partially differentiated mesenchymal stem cell, or any combination thereof.

The examples below specifically describe an injectable PEG-chitosan-graphene (PCG) hydrogel that enhances the differentiation of bone marrow derived mesenchymal stem cells (BM-MSC). The PCG hydrogel was synthesized by functionalizing graphene with chitosan. This was further acrylated to form an acrylated chitosan-graphene monomer and crosslinked with PEG-diacylate. The examples demonstrate that the PCG hydrogel owns high water content, uniform water distribution, and biodegradability, which were characterized by SEM, swelling kinetics, and DSC and biodegradation studies, respectively. The CalceinAM staining shows that incorporating graphene into the PCG hydrogel decreased the proliferation rate of BM-MSCs but increased the biocompatibility and positively influenced the differentiation of BM-MSCs.

The examples further show that even without differentiation media, the PCG hydrogel could induce osteogenesis and chondrogenesis. The adipogenic differentiation of BM-MSCs in PCG hydrogel with differentiation medium was much higher than PEG hydrogel or PC hydrogel under both hypoxia and normoxia according to the Oil Red O staining Based on the results of Alizarin red staining, the osteogenic differentiation of BM-MSCs was strongly enhanced in PCG hydrogel. Compared with normoxia, hypoxia seems to have no significant effect on the mineralization of BM-MSCs. The Alcian blue staining revealed a significant increase of glycosaminoglycan depositing on the PCG hydrogel under both normoxia and hypoxia conditions. All these results demonstrate that graphene-chitosan incorporated hydrogel can induce and further enhance the osteogenic and chondrogenic differentiation of BM-MSCs.

In some embodiments, the PCG hydrogel further comprises N-Isopropylacrylamide (NIPAM). Poly(N-isopropylacrylamide) (PNIPAM) undergoes a reversible discontinuous phase transition in water, changing from hydrophilic (swelling) to hydrophobic (shrinking) in response to a temperature change. Accordingly, PCG hydrogels that further incorporate NIPAM are referred to herein as TPCGs (thermosensitive PCGs). While this thermosensitive property of PNIPAM has been utilized in a switchable drug delivery system via incorporation of stimulus-sensitive materials, these prior art nanogels were not able to be maintained as stable nanoparticle dispersions without disturbing the thermosensitivity of the hydrogel matrix. Therefore, provided herein is a hydrogel composition comprising a graphene, a chitosan, a polyethylene (glycol) diacrylate (PEGDA), and an N-isopropylacrylamide (NIPAM). In some embodiments, the NIPAM is mixed and with PEGDA and acrylated chistosan-graphene for simultaneous covalent bonding of NIPAM and PEGDA to chitosan-graphene to form a TPCG. Further provided herein is a TPCG hydrogel composition further comprising a pharmaceutical composition.

It is a surprising finding of the present invention that a TPCG hydrogel can serve as a thermally inducible delivery vehicle for a pharmaceutical composition. The TPCG hydrogel provided herein provides clear advantages over other prior art materials that contain NIPAM. The low critical solution temperature (LCST) of pure PNIPAM gel crosslinked with N,N'-methylenebisacrylamide (BIS) was shown in the prior art to be 32-34° C. [Yavuz, M. S. et al., Nature Materials (2009) 8, 935; Shiotani, A. et al., Langmuir (2007) 23, 4012]. When the temperature was raised above 32° C., the polymer underwent a phase transition to a hydrophobic state, causing the gel to shrink. Thus, using the prior art PNIPAM hydrogel as the thermosensitive carrier for controlled drug release in vivo would result in a drug release state that would always be 'on.' The present invention solves the prior art problem by tuning the LCST of PNIPAM with the acrylated chitosan-graphene. In addition, the hydrophilic biocompatible crosslinker PEGDA was used instead of hydrophobic BIS.

The TPCG hydrogel provided herein shows significant reduction in size when temperature changed from 37° C. to 42° C. In accordance with the size change of TPCG upon heating, the turbidity of the TPCG also demonstrated the thermosensitve response. These results suggest that the TPCG remains swollen (in the 'off' state) at 37° C., but shrinks (in the 'on' state) above the phase transition temperature of 37° C.

For successful anticancer drug delivery, the drug carriers have to be constructed not only to respond to a specific stimulus but also to achieve a high drug loading capacity. For the reported light-triggered remote controlled drug delivery system, there has been little focus on drug loading capacity, even though drug loading capacity is a bottle-neck issue for the successful development of drug vehicles for potential clinical use [Shiotani, A. et al., Langmuir (2007) 23, 4012; Gorelikov, I. et al., J. of the American Chemical Society (2004) 126, 15938; Kang, H. Z. et al., Acs Nano (2011) 5, 5094]. Drug molecules can be incorporated into nanogels through chemical conjugation, physical entrapment during polymerization, or physical diffusion. Compared to the low bioavailability provided by chemical conjugation methods and the difficulty of purification when using physical entrapment methods, the physical diffusion method provided many advantages. The TPCG hydrogels of the present invention make use of physical diffusion methods.

The TPCG hydrogels provided herein deliver hydrophilic pharmaceutical compositions such as doxorubicin (DOX) by diffusion during the gel swelling process. A 48 wt % drug loading content can be achieved with the TPCG hydrogels, which percentage is significantly higher than the 26 wt % of pH sensitive pegylated nanogel or 16.14 wt % of mPEG-P (LG-LC) nanogel described in the prior art [Shi, F. H. et al., J. of Materials Chemistry (2012) 22, 14168; Oishi, M. et al., J. of Materials Chemistry (2007) 17, 3720]. The TPCG hydrogels also demonstrate thermosensitivity as shown in the examples below.

The confocal fluorescence images of TRC1 cells demonstrated that the DOX-TPCG was taken up by cells via the endocytic pathway and transported into the endosome. At 37° C., free DOX was observed in the nucleus after 60 minutes due to the binding of DOX to the nuclear DNA. The fluorescence of DOX-TPCG was only seen in the cytoplasm after 60 minutes, which indicates that DOX is still trapped inside the TPCG particles because of the swollen state at 37° C. At 42° C., the fluorescence intensity in cells was increased for both free DOX and DOX-TPCG after 30 minutes. The reason for the higher DOX levels in cells at 42° C. is unknown, but presumably it is due to increased cellular endocytosis, which has been shown to be both energy- and temperature-dependent. In addition, the fluorescence intensity in the nucleus was increased for both free DOX and DOX-TPCG. These results suggest that DOX was released from the TPCG in the endosome and transported to the nucleus owing to the shrinkage of the nanogel upon heating.

Further, the cytotoxicity of DOX-TPCG was much less than free DOX at 37° C. but comparable to free DOX at 42° C. The empty TPCG was not toxic to cells, and heating of cells to 42° C. for 30 minutes did not reduce cell viability. Therefore, the increased cytotoxicity of DOX-TPCG was owing to the faster DOX release from the endosome. This enhancement of cytotoxicity of DOX-TPCG result is in accordance with the result of DOX release behavior from DOX-TPCG inside the cells.

In summary, the TPCG hydrogel provided herein is a uniformly dispersed thermosensitive graphene nanogel, which showed a dramatic size change when the temperature was increased from 37° C. to 42° C. The turbidity test showed that the thermosensitivity of TPCG is reversible. The TPCG is not toxic to cells at 37° C. or 42° C. The thermosensitive DOX-TPCG demonstrated more drug release at 42° C. than 37° C. demonstrating its switchable drug release behavior. When added to cells, DOX-TPCG stayed in the cytoplasm at 37° C., but at 42° C. DOX was released and entered the nucleus. The thermosensitive release profile of DOX-TPCG was further confirmed by the anti-proliferative activity test, which showed more toxicity at 42° C. than 37° C. Collectively, these results show that the TPCG provided herein has the potential for noninvasive remote-controlled drug release triggered by exposure to light from a near infrared (NIR) laser. Upon exposure to the NIR laser, light will be absorbed and converted to heat through the photothermal response of graphene, which will raise the temperature of the nanogel, causing it to shrink and release the drug. When the laser is turned off, the drop in temperature allows the nanogel to return to its swollen state, thereby stopping release of the pharmaceutical composition contained within the TPCG hydrogel.

Accordingly, further provided herein is a method of delivering a pharmaceutical composition to a cell comprising administering to the cell a TPCG hydrogel and the pharmaceutical composition and subsequently increasing the temperature of the TPCG hydrogel to at or above a TPCG phase change temperature. The TPCG phase change temperature can be approximately 35° C., 36° C., 37° C., 38° C., 39° C., 40° C., 41° C. or 42° C. In one embodiment, the TPCG phase change temperature is approximately 37° C. It should be understood that the increase in temperature can be achieved by any means known to one of ordinary skill in the art. In one embodiment, the increase in temperature is achieved through the use of a near infrared laser.

The PCG and TPCG hydrogels provided herein can be administered to a subject for treatment of a disease or condition. The hydrogels of the present invention can be administered via any route. Examples of administration routes include oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via implantation. The term "parenteral" includes subcutaneous, intravenous, intramuscular, intra-articular, intra-synovial, intrasternal, intrathecal, intrahepatic, intralesional, and intracranial injections or infusion techniques.

In one embodiment, a PCG hydrogel further comprising a mesenchymal stem cell, a wholly or partially differentiated mesenchymal stem cell, or any combination thereof, is administered to a subject for the treatment of a condition including, but not limited to, treatment of damaged tissue and/or inflammation resulting from cardiovascular disease or myocardial infarction (MI), brain or spinal cord injury, stroke, diabetes, cartilage or bone injury, Crohn's disease, or graft versus host disease (GvHD). The terms "treat," "treating," "treatment," and grammatical variations thereof as used herein include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially.

It should be understood that the mesenchymal stem cells comprised within the PCG hydrogel can be obtained from the same subject to which they are later administered. For example, in one embodiment, mesenchymal stem cells are obtained from a subject and then contacted or placed within a PCG hydrogel in vitro for a given period of time to allow for differentiation, and subsequently the PCG hydrogel containing differentiated cells is administered back to the subject. Accordingly, provided herein is a method of differentiating mesenchymal stem cells comprising contacting the cells with a hydrogel composition comprising a graphene, a chitosan, and a polyethylene (glycol) diacrylate (PEGDA). The mesenchymal stem cells can be placed or seeded into the PCG hydrogel for a period of time between approximately 1 hour and 14 days. In some embodiments, the mesenchymal stem cells are placed or seeded into the PCG hydrogel for a period of approximately 1, 2, 3, 4, 5, 6, 7, 8, 9, 10, 11, 12, 13, or 14 days. In other embodiments, mesenchymal stem cells can be placed or seeded into the PCG hydrogel for a period of approximately 1, 2, 3, 4, 5, 6, 7, 8, 9, 10, 11, 12, 18, or 24 hours.

In another embodiment, a TPCG hydrogel further comprising a hydrophobic pharmaceutical composition is administered to a subject for the treatment of a disease or condition such as cancer. The pharmaceutical composition can comprise any pharmaceutical suitable for treatment. In one embodiment, the pharmaceutical is doxorubicin. In these embodiments, administration of a TPCG hydrogel further comprising a pharmaceutical composition can be followed by thermal activation of the TPCG hydrogel. In some embodiments, thermal activation is accomplished by applying an infrared light source to the region surrounding the hydrogel after the hydrogel is administered to a subject.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. All patents, patent applications, and publications referenced herein are incorporated by reference in their entirety for all purposes.

EXAMPLES

Example 1

Preparation and Characterization of PCG Hydrogel

A PCG hydrogel was prepared based on a chitosan modified graphene and poly(ethylene glycol) (PEG) according to FIG. 1 (A-E). To increase the carboxylic acid groups on the surface of graphene sheets, graphene oxide was first reduced to graphene and then reacted with $ClCH_2COOH$. Chitosan was covalently bonded to graphene via amide bond by reacting the amine groups of chitosan with the COOH groups of graphene in the presence of EDC and NHS. The chitosan functionalied graphene was further reacted with acrylic acid to form an acrylated chitosan-graphene monomer which was crosslinked with PEGDA to form PEG-Chitosan-Graphene hydrogel.

More specifically, the following materials were used: Graphene oxide 0.5% water solution (Angstron Materials Inc., OH, USA), water soluble chitosan (Mw, 10 kDa) was donated from Transgenex Nanobiotech Inc. Poly (ethylene glycol) diacrylate (PEGDA), Tetramethylethylenediamine (TEMED), Ammonium persulphate (APS), acrylic acid anhydrous, ethyl (dimethylaminopropyl) carbodiimide (EDC), and N-Hydroxysuccinimide (NHS).

To prepare acrylated-Chitosan graphene, graphene-COOH was prepared according to the reported procedure with minor modification. PSS-coated reduced graphene oxide (GO) sheets were prepared by reduction of GO (1 mg/mL) in the presence of poly(sodium 4-styrenesulfonate) (PSS) (15 mg/mL) and 1.5 ml hydrazine under refluxing at 100° C. [Stankovich, S. et al., Nature (2006) 442, 282]. After cooling down to room temperature, NaOH (1.2 g) and chloroacetic acid ($ClCH_2COOH$) (1.0 g) were added to the GO-PSS solution and sonicated for 3 hours [Sun, X. et al., Nano Research (2008) 1, 203] to convert the OH groups to COOH via conjugation of acetic acid moieties giving graphene-COOH.

Chitosan-graphene was then prepared as follows. One ml graphene-COOH suspension (1.28 mg graphene) was activated with EDC (30 mg) and NHS (30 mg) in 1 ml water for 30 minutes, and added to water soluble chitosan solution (150 mg in 10 ml water). The reaction was kept for 3 hours before dialyzing with 1000 molecular weight cutoff dialysis bag for 2 days. Finally, acrylated-chitosan-graphene was prepared by adding EDC and NHS activated acrylic acid (10 µl) to the chitosan-graphene solution. After reacting for 3 hours, the solution was purified by dialysis with 12-14 k molecular weight cutoff dialysis bag for 2 days. The purified solution was lyophilized.

Acrylated chitosan was prepared by adding EDC and NHS activated acrylic acid (10 ul) to 10 ml chitosan solution (150 mg). The purification procedure was the same as the acrylated chitosan-graphene.

Then 450 µl of 1 mg/ml of acrylated chitosan-graphene solution was added to 2 ml centrifuge tube with 956 µl de-ionized water. 45 µl of 10 wt % APS and PEG-diacrylate was added to the tube and vortexed to mix well. The solution was purged with argon gas for 30 seconds. 4 µl of TEMED was added to the solution and vortexed for 1 second. 75 µl of the solution was added to each well of the 96-well plates. The solution was left for 5 min to form the graphene-chitosan-PEG (GCP) hydrogel. The PEG hydrogel and Chitosan PEG hydrogel as control were prepared the same way but without acrylated chitosan-graphene solution or with acrylated chitosan instead of acrylated chitosan-graphene solution. After forming the hydrogel, 200 µl of deionized water was added to each well to wash the hydrogel every 2 hours for one week. Before the cells were plated onto hydrogel, the hydrogel was washed one time with PBS and one time with DMEM and sterilized for 2 hours with UV.

Figure 2:
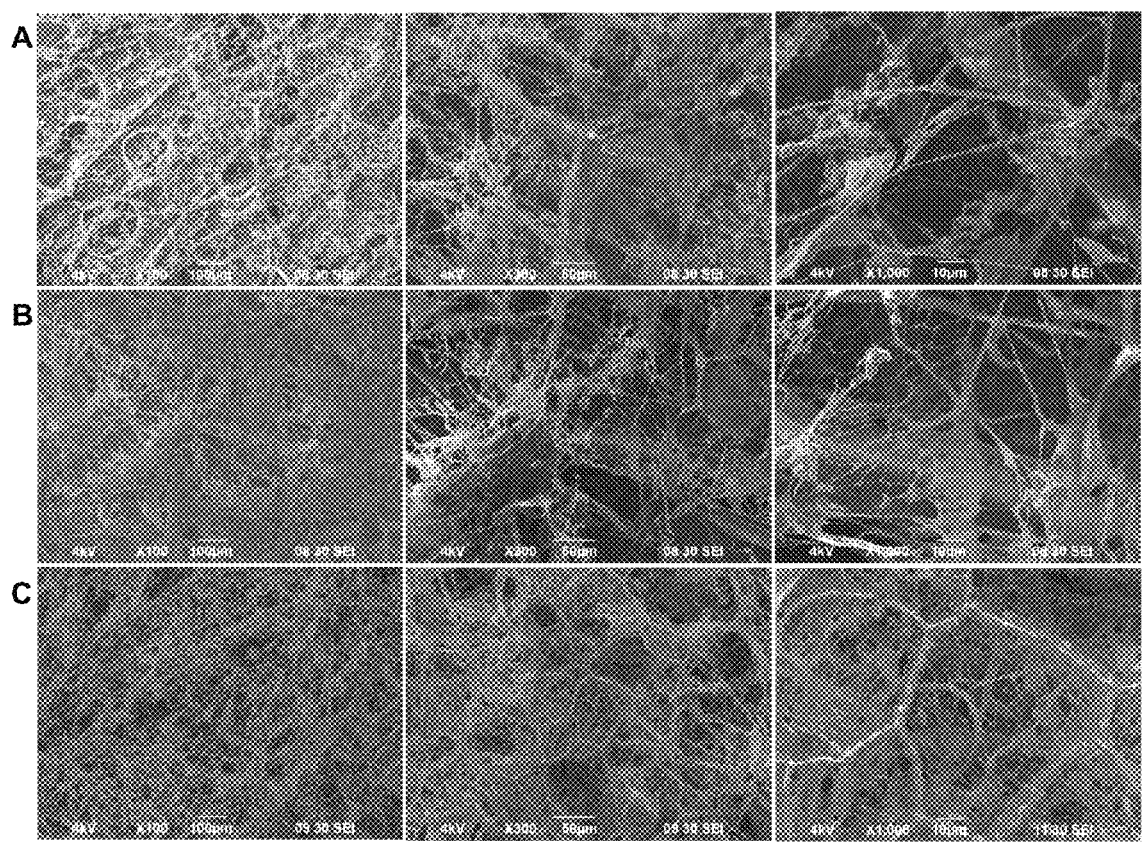
FIG. 2 (A-C) shows SEM micrographs with different magnifications of freeze-dried (A) PEG hydrogel, (B) PC hydrogel, and (C) PCG hydrogel.

To test the inner morphology by SEM, hydrogel samples were cut to 10 µm thick and freeze-dried. The morphology of the freeze-dried gels was studied via a Jeol SEM. FIG. 2 shows the cross-section morphology of PEG hydrogel, PEG-chitosan hydrogel and PEG-chitosan-graphene hydrogel. The inner morphology of PEG, chitosan-PEG, and graphene-chitosan-PEG hydrogel shows well defined and interconnected spider net-like structure on the surface of the pores. The microarchitecture of the hydrogel is very similar to the extracellular matrix (ECM). PEG hydrogel and PEG-chitosan hydrogel demonstrate some big pieces of plates between the nets. Compared to the PEG-chitosan hydrogel, the morphology of PEG-chitosan-graphene hydrogel is more net-like and uniformly dispersed. It indicates that the presence of graphene inside the hydrogel could enable the microarchitecture to be more uniform and more porous, which will be a benefit for the transported nutrients.

The swelling rate of PEG hydrogel, PEG-Chitosan hydrogel and PEG-Chitoan-Graphene hydrogel were determined as follows: Hydrogel samples were freeze-dried for one day and stored in a desiccator at room temperature. The sorption behavior of hydrogels was monitored by detecting the increase in mass of the samples at different time intervals by a balance. In a typical sorption experiment, a pre-weighed dry gel sheet was immersed in water at 24±1° C. water bath. At prescribed time intervals, the hydrogel was taken out of solution and weighed after wiping off the excess water from the surface with Kimwipe paper (Kimberly Clark Professional). The sorption degree, SD, of hydrogels was defined as follows: SD %=$(W_t-W_d) \times 100/W_d = M_t \times 100/W_d$ where $W_d$ is the weight of the dry gel, $W_t$ is the weight of wet hydrogel at each time interval, and $M_t$ is the gain in the weight of the dry gel at time t.

Figure 3:
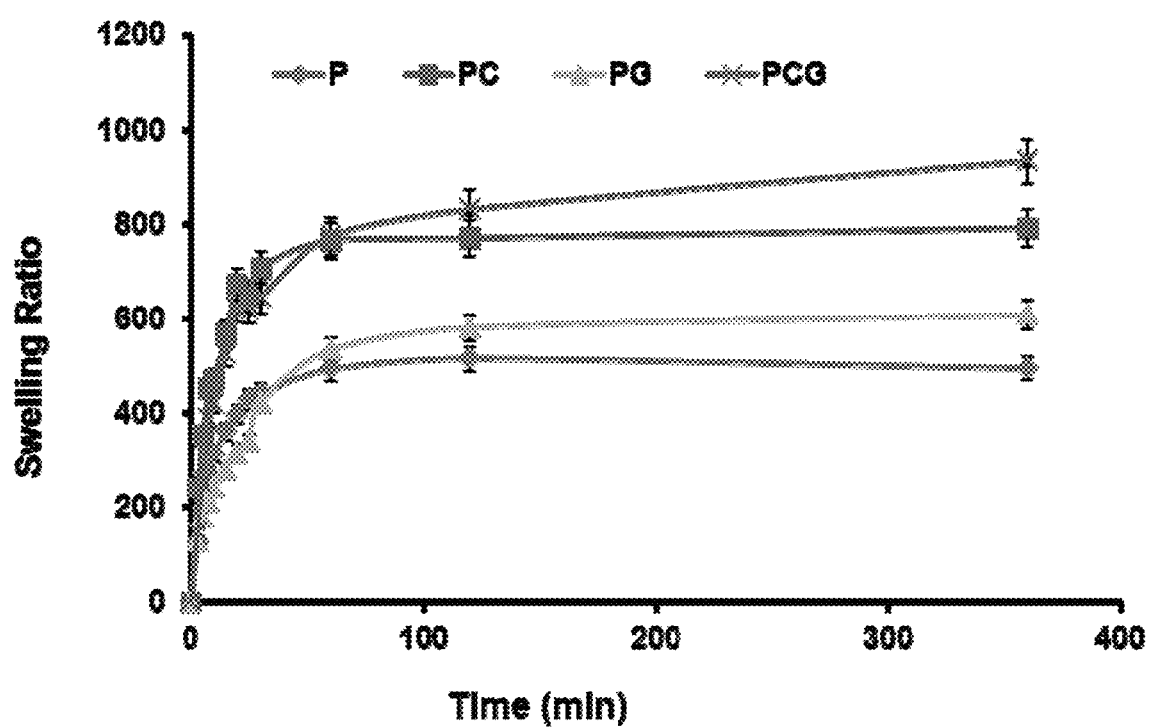
FIG. 3 is a graph showing the swelling kinetics for PEG hydrogel (P), PC hydrogel, PG hydrogel, and PCG hydrogel.

The results of the sorption analyses are shown in FIG. 3. The swelling rate of all three hydrogels was fast at the beginning and then leveled off. PEG hydrogel achieved equilibrium within 1 hour, but PEG-Chitosan and PEG-Chitosan-Graphene achieved equilibrium within 3.5 hours. Accordingly, it took a longer time to arrive at the swelling equilibrium for PEG-chitosan hydrogel and PEG-Chitosangraphene hydrogel. The equilibrium swelling degree of Chitosan-PEG hydrogel is higher than PEG hydrogel. The amino groups of the chitosan are hydrophilic, which will atrract more water to hydrogel.

The equilibrium swelling degree of PEG-chitosan-graphene hydrogel is much higher than chitosan-PEG. It was reported that the swelling capacity of the hydrogel exhibited significant improvement when graphene oxide content inside the P(AA-co-AM) hydrogel increased from 0 to 0.1% [Huang, Y. et al., Colloids and Surfaces a-Physicochemical and Engineering Aspects (2012) 401, 97]. The GO/PVA with 0.6% GO among 0.0, 0.2%, 0.4%, 0.6% GO/PVA hydrogel has the highest maximum swelling ratio [Zhang, L. et al. J. of Materials Chemistry (2011) 21, 10399]. The hydrogel described herein contains approximately 0.08 wt % graphene and demonstrated a trend similar to the reported results. The improvement of swelling capacity of the low graphene containing hydrogel might be due to the high density of hydrophilic groups on the surface of the graphene sheet, the homogenously dispersed graphene sheet influencing the microstructure of polymer network, or some synergetic intermolecular interactions between GO sheets and polymer networks for holding water [Huang, Y. et al., Colloids and Surfaces a-Physicochemical and Engineering Aspects (2012) 401, 97].

The crystallization process of water inside the hydrogel was complicated and related to the water content of hydrogel. Water inside of a hydrogel can be classified into non-freezing, freezing bound and free water according to the phase transition, and molecular mobility of the water can be tested by NMR, TGA, FTIR and DSC [Yoshida, H. et al., J. of Thermal Analysis (1993) 40, 483; Wang, C. et al., Biomacromolecules (2008) 9, 561]. The non-freezing water forms hydrogen bonds with polymer chains, which are immobilized and show no freezing peak even up to $-100°$ C. Freezing bound water interacts weakly with polymer molecules and has a melting endotherm below 0° C. Free water does not take part in hydrogen bonding with polymer chains and behaves similarly with pure water.

Figure 4:
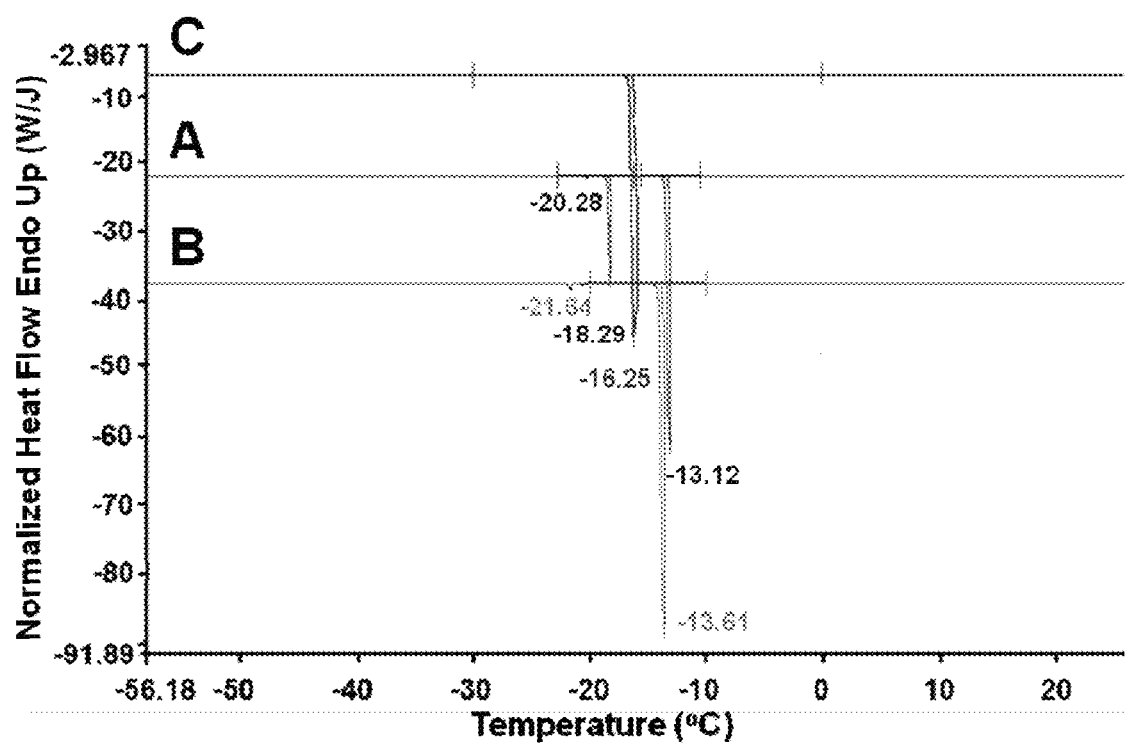
FIG. 4 is a graph showing the DSC cooling curves of (A) PEG hydrogel, (B) PC hydrogel, and (C) PCG hydrogel.

FIG. 4 shows the schematic DSC cooling curves of the equilibrium swollen PEG hydrogel, PEG-chitosan hydrogel and PEG-chitosan-graphene hydrogel. Three exothermic peaks (sharp big at $-13.12°$ C., sharp medium at $-18.29°$ C., small at $-20.28°$ C.) of crystallization were observed during the cooling process of equilibrium swollen PEG hydrogel. Two exothermic peaks (sharp at $-13.61°$ C., tiny at $-21.64°$ C.) were observed on the equilibrium swollen PEG-Chitosan hydrogel cooling curve. However, the PCG hydrogel cooling curve only showed one sharp big peak at $-16.25°$ C., which is lower than the first peak of PEG or PEG-Chitosan. Since the rate of crystallization of freezing bound water is slower than that of free water, the crystallization at $-18.29°$ C., $-20.28°$ C. and $-21.64°$ C. represents the freezing bound water in the form of metastable ice and the crystallization at $-13.12°$ C. and $-13.61°$ C. represents the free water in the form of stable hexagonal ice. In equilibrium swollen PCG hydrogel, the crystallization of free water seems to be delayed and freezing bound water seems to be early such that they are merged together to form one sharp peak.

Figure 5:
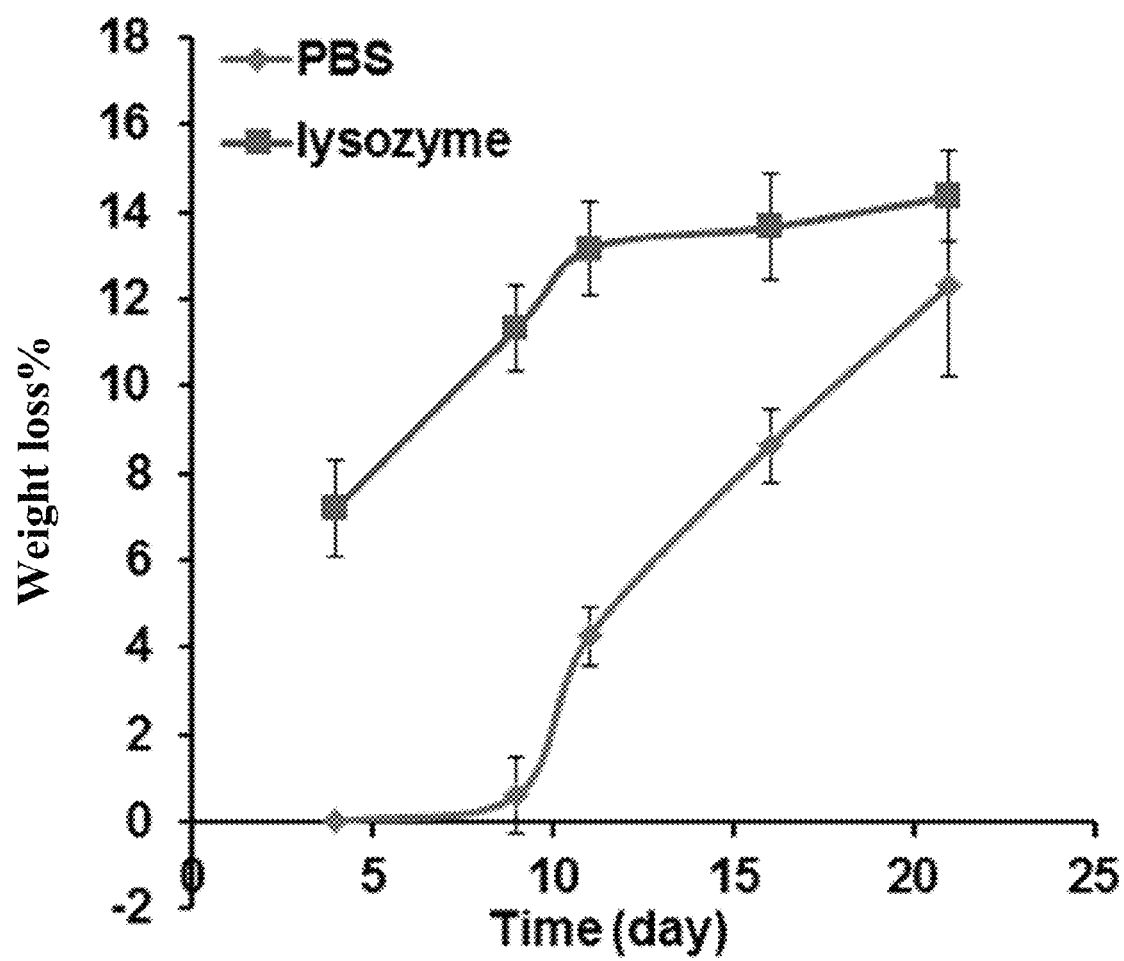
FIG. 5 is a graph showing the degradation degree of PCG hydrogel after 3 weeks of incubation with 0.1 M PBS or 1 mg/ml lysozyme at 37° C.

In tissue engineering, the regeneration of the tissue is accompanied by the degradation of the supporting matrix for the implanted cells. The degradation rate of matrix can affect the restoration of the tissue: matrix degradation that is too quick could release cells and matrix components, while matrix degradation that is too slow could inhibit matrix production and assembly [Bahney, C. S. et al., Faseb Journal (2011) 25, 1486]. Chitosan degrades slowly in vitro in PBS, but degradation rate will be accelerated in the presence of the lysozyme, which is the primary enzyme responsible for in vivo degradation of CS through hydrolysis of the glycosidic bonds [Hong, Y. et al., Acta Biomaterialia (2007) 3, 23; Freier, T. et al., Biomaterials (2005) 26, 5872]. To mimic the in vivo degradation performance, the degradation kinetics of the PCG hydrogel was examined in the presence of lysozyme under accelerated conditions compared to the PBS (FIG. 5). The degree of degradation was estimated in terms of change of dry weight of the hydrogel. Gels were incubated in 0.1 M PBS (pH7.4) or 1 mg/ml lysozyme PBS solution at 37° C. for the duration of 21 days. In 3 days, there is no degradation in PBS and 7% loss in lysozyme. In 9 days, there is only 1% weight loss in PBS but an 11% loss in lysozyme. After 9 days the degradation rate increased in PBS but slowed down in lysozyme. The degradation behavior of PCG hydrogel in lysozyme is in accordance with the reported results of PEG cross linked chitosan hydrogel film [Tanuma, H. et al., J. of Applied Polymer Science (2009) 114, 1902].

Example 2

Cell Viability and Morphology of Cells Placed on a PCG Hydrogel

The cell morphology on the monolayer, PEG hydrogel, PC hydrogel, PG, and PCG hydrogel was investigated with Calcein AM staining (data not shown). The cells cultured on monolayer form a spindle-shape. On four hydrogels the cells are fine and form the rounded shape. The proliferation rates of BM-MSC on PG and PCG hydrogel decreased compared to PEG and PC hydrogels. There are two possible reasons for this observation: (1) graphene is cytotoxic or (2) BM-MSCs differentiate into other lineages because of the unique properties of the graphene incorporated into the hydrogel. From the EthD-1 staining, it can be seen that BM-MSCs on graphene incorporated hydrogel PG and PCG is more biocompatible than PEG or PC hydrogel. This indicates that the cytotoxicity of graphene is not the main reason for the lower proliferation rate of BM-MSCs on graphene incorporated hydrogel. The big nodules and connection between nodules was also observed on PCG hydrogel, which indicate the interaction between cell-cell or cell-substrate.

Example 3

Adipogenic Differentiation of Cells Placed on a PCG Hydrogel

Figure 6:
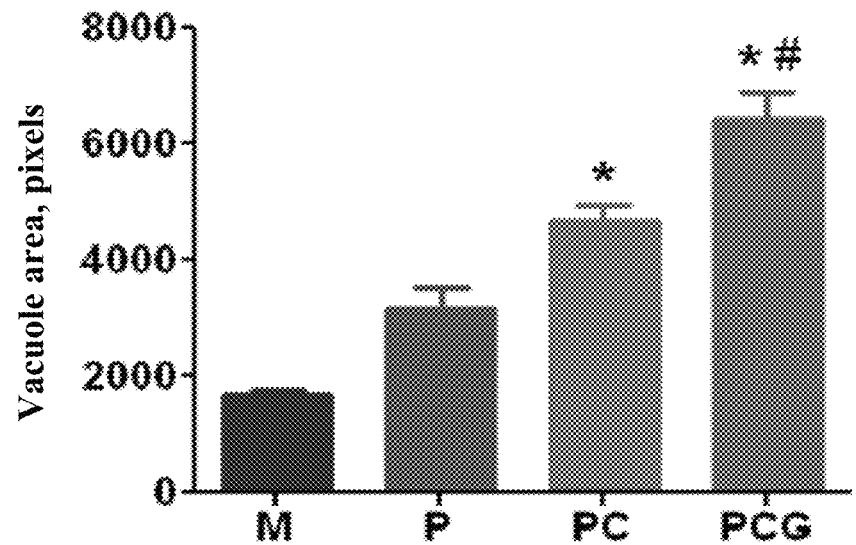
FIG. 6 is a graph showing adipogenesis of BM-MSCs with induction under nomoxia. More vacuoles were found in adipocytes differentiated in PCG hydrogel. The area of fat vacuole per cell was quantified with imageJ after mouse MSCs were cultured overnight on three different hydrogels in a 96-well plate. From the second day, adipocyte differentiating medium was added to the cells under nomoxia. On the seventh day, the cells were stained with Oil red O. M=monolayer, P=PEG hydrogel, PC=PC hydrogel, and PCG=PCG hydrogel. Cells from 4 fields/group were analyzed. #$p<0.01$; PEG vs Graphene. *$p<0.05$; PC vs PCG.
Figure 7:
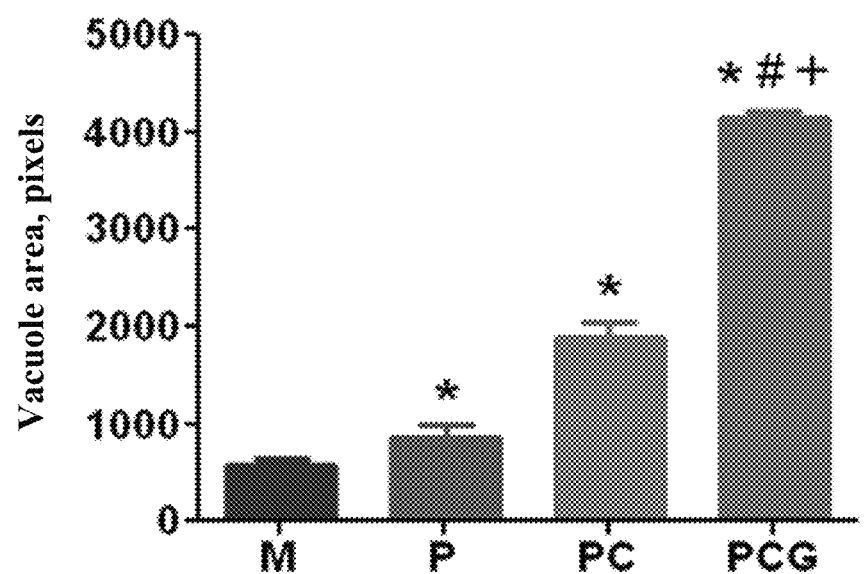
FIG. 7 is a graph showing adipogenesis of BM-MSCs with induction under hypoxia. More vacuoles were found in adipocytes differentiated in PCG hydrogel. Mouse MSCs were cultured overnight on three different hydrogels in a 96-well plate. From the second day, adipocyte differentiating medium was added to the cells under hypoxia. On the seventh day the cells were stained with Oil red O. M=monolayer, P=PEG hydrogel, PC=PC hydrogel, and PCG=PCG hydrogel. Area of fat vacuole per cell was quantified with imageJ. Cells from 4 fields/group were analyzed. #$p<0.01$; PEG vs Graphene. *$p<0.05$; PC vs PCG.

The adipogenic differentiation of MSCs on the hydrogels described herein was determined by specifically staining intra-cytoplasmic lipids with Oil Red O and quantifying these lipids by normalizing the total area of lipid droplets per cell. Without the differentiation medium, no adipogenesis was observed on the hydrogel (data not shown). Compared to a monolayer, 3D hydrogel demonstrated intensive staining Compared to the PEG hydrogel and PEG-chitosan hydrogel, the PCG hydrogel showed the most lipid droplets and exhibited the highest levels of oil red O staining See FIG. 6. Accordingly, graphene incorporated into 3D hydrogel significantly enhanced the adipogenic differentiation instead of inhibiting such differentiation as seen with graphene materials in the prior art. These results suggest potential applications of graphene-chitosan-PEG hydrogel for adipose tissue regeneration. FIG. 7 also demonstrates that the PCG hydrogels support adipogenic differentiation of MSCs under hypoxic conditions.

Example 4

Osteogenic Differentiation of Cells Placed on a PCG Hydrogel

Implanting biocompatible and biodegradable hydrogel with BM-MSCs cells is a promising approach for repairing bone fractures. However, the clinical application of this technique is limited by the differentiation gap. Therefore, it is of critical importance to develop a 3D hydrogel matrix that can promote the differentiation of BM-MSCs.

In this study, the influence of the graphene on the osteogenic differentiation of BM-MSCs in hydrogel was investigated by plating mouse BM-MSCs on PCG hydrogel. The osteogenic differentiation of BM-MSCs was evidenced by the accumulation of calcium or an increase in alkaline phosphatase, which is an early marker of osteogenesis. Without induction under normoxia, the osteogenesis of BM-MSCs was only observed on PCG hydrogel (data not shown). This result indicated that the nanostructure of the graphene and chitosan can induce the osteogensis of BM-MSC.

Figure 8:
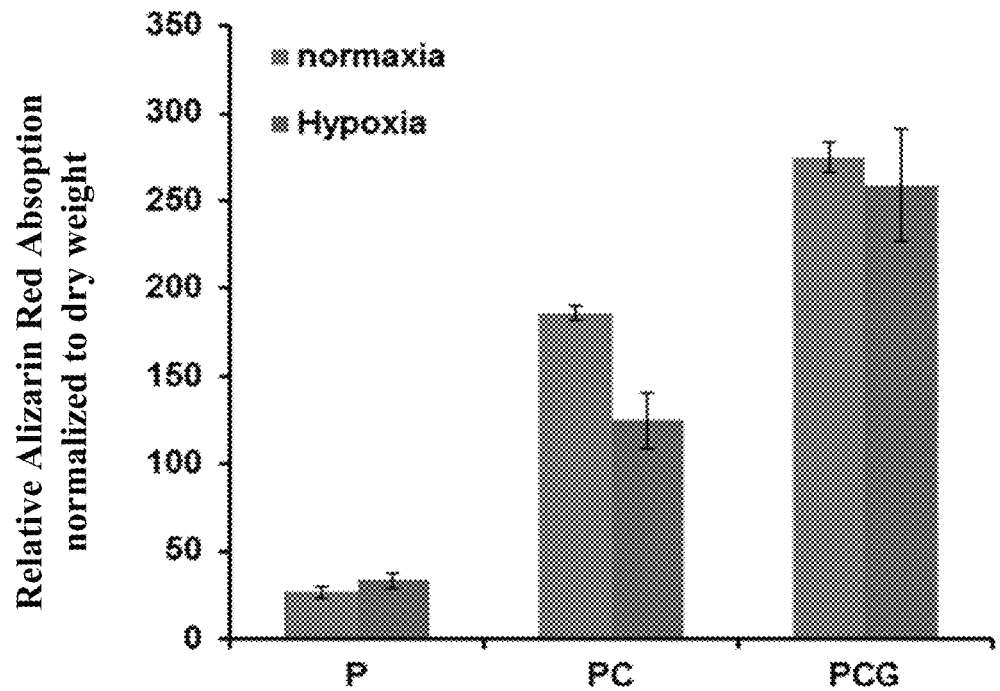
FIG. 8 is a graph showing osteogenesis of BM-MSCs with induction under normoxia and hypoxia. Osteogenic differentiation of BM-MSC was first visualized by staining at normoxia and hypoxia conditions after 7 days of incubation on hydrogels. Alizarin Red quanitification was performed by UV-vis absorption and normalized to the dry weight of hydrogel and cells. M=monolayer, P=PEG hydrogel, PC=PC hydrogel, and PCG=PCG hydrogel.

After 7 days of osteogenic induction, the extent of mineralization of MSCs cultured on PEG hydrogel, PEG-Chitosan hydrogel and graphene-chitosan-PEG hydrogel was assessed via Alizarin Red S staining of calcium as shown in FIG. 8. It was found that extent of mineralization in the MSCs cultured on graphene-chitosan-PEG hydrogel is greater than that cultured on PEG hydrogel or Chitosan-PEG hydrogel. This result indicated that graphene in the hydrogel could enhance the osteogenic differentiation of BM-MSCs. Spectrophotometric quantification confirmed these observations, with significantly higher absorbance at 480 nm for BM-MSC on PEG-chitosan-graphene hydrogel compared to that on PEG hydrogel and PEG-chitosan hydrogel (data not shown). This represents a 6-fold increase in the extent of mineralization in the BM-MSC cultured on PEG-chitosan-graphene hydrogel compared to PEG hydrogel.

Osteogenic differentiation and mineralization of bone marrow stromal (BMS) cells usually depends on the cells' interactions with bioactive peptides associated with the matrix proteins. The RGD peptides of ECM proteins interact with BMS cells through integrin surface receptors to facilitate cell spreading and adhesion. The BMP peptide corresponding to residues 73-92 of bone morphogenetic protein-2 promotes differentiation and mineralization of BMS cells. In the prior art, RGD peptide or BMP peptide had to be incorporated into a hydrogel to facilitate osteogenic differentiation of BM-MSCs [He, X. Z. & Ma, J. Y., Langmuir (2008) 24, 12508; Roostaeian, J. et al., J. of Surgical Research (2006) 133, 76]. However, the PCG hydrogel described herein did not require the addition of either of these peptides in order to facilitate osteogenic differentiation of BM-MSCs.

The minerals formed within the PCG hydrogel matrix were further visualized using SEM (data not shown). The morphology of minerals deposited within the hydrogel was imaged with scanning electron microscopy (SEM). Calcium phosphate particles were extensively deposited on the surface of cells and the PCG hydrogel matrix.

When transplanted in vivo, human MSCs cells will be exposed to low oxygen concentration since physiological oxygen tension in a bone fracture is very low (i.e. 1% $O_2$) due to the disruption of the host vascular system [Potier, E. et al., Bone (2007) 40, 1078; Brighton, C. T. & Krebs, A. G. J. of Bone and Joint Surgery-American Volume A (1972) 4, 323; Heppenstall, R. B. et al., Clinical Orthopaedics and Related Research (1975) 357]. Therefore, it is of great importance to investigate the osteogenic differentiation of implanted MSCs in hydrogel under hypoxic conditions. FIG. 8 shows the osteogenic differentiation of BM-MSC under hypoxic conditions. PCG hydrogel was the most densely stained compared to PEG hydrogel and PC hydrogel. Compared with normaxia, hypoxia seems to have no significant effect on the mineralization of MSC.

The results provided herein are different from data previously reported. Previously, it was found that osteogenic differentiation of mouse BM-MSC or hMSC was inhibited at 3% oxygen [Potier, E. et al., Bone (2007) 40, 1078; Panyukhin, N. V. et al., Biologicheskie Membrany (2008) 25, 352; Fehrer, C. et al., Aging Cell (2007) 6, 745]. Potier et al. reported that temporary exposure of MSCs to hypoxia leads to some osteogenic genes being downregulated and implied that exposure of MSCs transplanted in vivo to hypoxia may affect their bone forming potential [Potier, E. et al., Bone (2007) 40, 1078]. However, the data provided herein indicates that a PCG hydrogel could preserve the full osteogenic potential of BM-MSCs for in vivo applications.

Example 5

Chondrogenic Differentiation of Cells Placed on a PCG Hydrogel

The cartilage tissue is a flexible connective tissue composed of chondrocytes in an abundant extracellular matrix (ECM) that is mainly composed of collagen type II, proteoglycan, and aggrecan. Due to the intrinsic biology of cartilage tissues, such as limited blood supply and lack of self-regeneration capacity, current treatment of cartilage lesions are not sufficient to restore normal function [Bhardwaj, N. & Kundu, S. C. Biomaterials (2012) 33, 2848]. Stem cell-based tissue engineering represents a promising approach for the repair of cartilage. However, the prior art provides no ideal scaffold for this approach.

Accordingly, the effect of PCG hydrogel on the chondrogenic differentiation of BM-MSC and hMSCs was determined. The process of chondrogenic differentiation of MSCs involves condensation of progenitors, chondrocyte differentiation, and deposition of cartilaginous extracellular matrix (ECM), resulting in the formation of cartilage during chondrogenesis. The chondrogenic differentiation was estimated by Alcian blue staining of the glycosaminoglycans (GAG) present in aggrecan, which forms the major component of extra cellular matrix of the cartilage.

Figure 9:
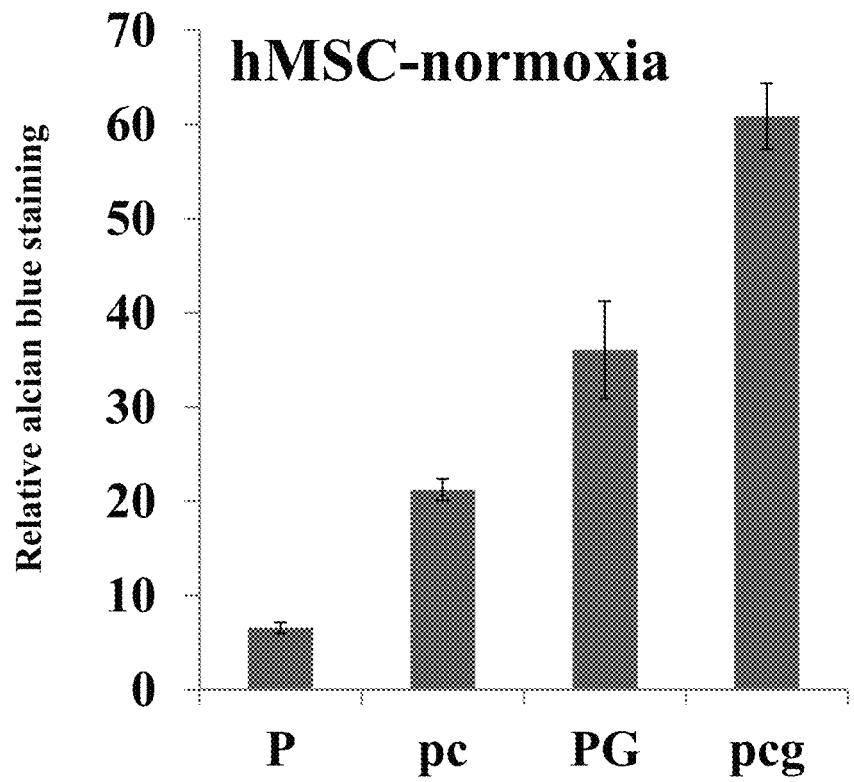
FIG. 9 is a graph showing chondrogensis of hMSCs with induction under normoxia. 40k hMSCs were cultured overnight in growth medium on different hydrogels in a 96-well plate under normoxia conditions. On the second day, the growth medium was replenished with differentiation medium. On the seventh day, the cells were stained with alcian blue stain, and area of alcian blue was quantified with imageJ. The differentiation was well defined and sGAG were upregulated on PCG hydrogel when compared to the other hydrogels. M=monolayer, P=PEG hydrogel, PC=PC hydrogel, and PCG=PCG hydrogel.
Figure 10:
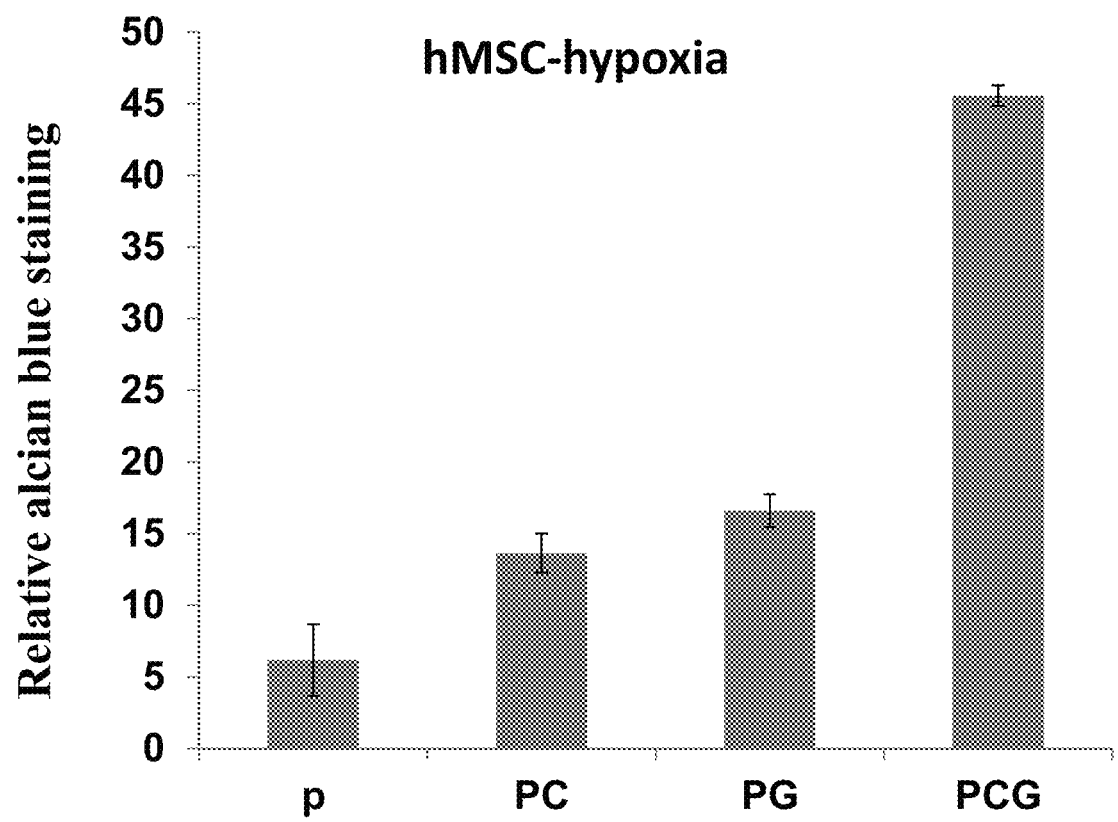
FIG. 10 is a graph showing chondrogensis of hMSCs with induction under hypoxia. 40k hMSCs were cultured overnight in growth medium on different hydrogels in a 96-well plate under hypoxia conditions. On the second day, the growth medium was replenished with differentiation medium. On the seventh day, the cells were stained with alcian blue stain, and area of alcian blue was quantified with imageJ. The differentiation was well defined and sGAG were upregulated on PCG hydrogel when compared to the other hydrogels. M=monolayer, P=PEG hydrogel, PC=PC hydrogel, and PCG=PCG hydrogel.

The BM-MSCs and hMSCs that were grown on PCG hydrogel show the most intense blue staining as compared to PEG hydrogel, PC hydrogel and PG hydrogel. These results indicate that chitosan-graphene induces more deposition of glycosaminoglycan and promotes chondrogenic differentiation. FIG. 9 provides a graph showing the results obtained with hMSCs. As shown in FIG. 10, the proteoglycan deposition on PCG hydrogel under hypoxia conditions was significantly greater than that observed under normoxic conditions. The effect of hypoxia on the chondrogensis of stem cells is dependent on the stem cells type. Hypoxia promotes chondrogenesis in rat mesenchymal stem cells, human embryonic stem cells, and stem cells from the infrapatellar fat pad of osteoarthritis patients [Koay, E. J. & Athanasiou, K. A. Osteoarthritis and Cartilage (2008) 16, 1450; Kanichai, M. et al., J. of Cellular Physiology (2008) 216, 708; but inhibits chondroprogenitor lineage differentiation of adipose-derived mesenchymal cells [Malladi, P. et al., American J. of Physiology-Cell Physiology (2006) 290, C1139].

Example 6

Preparation and Characterization of TPCG Hydrogel

Figure 11:
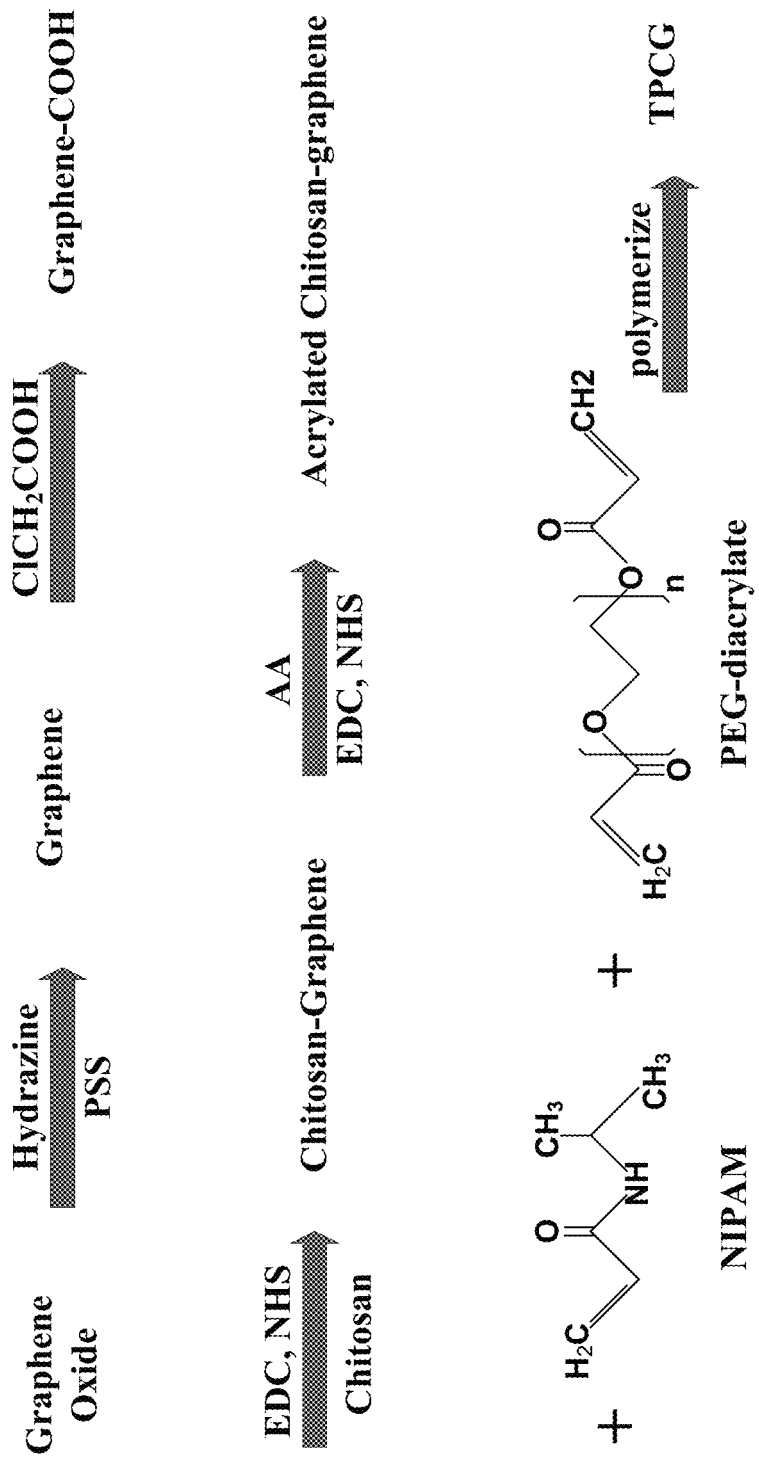
FIG. 11 is a schematic of TPCG hydrogel synthesis.

A TPCG hydrogel was prepared based on a chitosan modified graphene and poly(ethylene glycol) (PEG) according to FIG. 11. To increase the carboxylic acid groups on the surface of graphene sheets, graphene oxide was first reduced to graphene and then reacted with $ClCH_2COOH$. Chitosan was covalently bonded to graphene via amide bond by reacting the amine groups of chitosan with the COOH groups of graphene in the presence of EDC and NHS. To prevent coagulation, the chitosan functionalized graphene sheet was further reacted with acrylic acid to obtain the acrylated chitosan-graphene monomer. The acrylated chitosan-graphene monomers were copolymerized with NIPAM and PEGDA to form a nanogel instead of being physically dispersed inside the gel. More specifically, the following materials and methods were used.

Materials

Graphene oxide 0.5% water solution was purchased from Angstron Materials Inc., OH, USA. Water soluble chitosan (Mw 10 kDa) was donated by Transgenex Nanobiotech Inc. Poly(sodium 4-styrenesulfonate) (PSS, Mw 70,000), N-Isopropylacrylamide (NIPAM), acrylic acid anhydrous, polyethylene glycol-diacrylate (PEGDA), ethyl(dimethylamino-propyl)carbodiimide (EDC), N-Hydroxysuccinimide (NHS) were bought from Sigma-Aldrich (St Louis, Mo., USA).

Preparation of Graphene-COOH with Acrylated Chitosan

To prepare graphene-COOH, graphene-COOH was prepared according to the reported procedure with minor modification. PSS-coated reduced GO sheets were prepared by reducing 50 ml GO (1 mg $mL^{-1}$) in the presence of PSS (15 mg $mL^{-1}$) and 1.5 ml hydrazine under refluxing at 100° C. [Stankovich, S. et al., Nature (2006) 442, 282]. After cooling to room temperature, 1.2 g NaOH and 1.0 g chloroacetic acid were added to the GO-PSS solution and sonicated with 2510 Branson sonicator for 3 hours [Sun, X. et al., Nano Research (2008) 1, 203] to convert the OH groups to COOH via conjugation of acetic acid moieties, giving graphene-COOH.

To conjugate chitosan to the graphene-COOH, 1 mg/ml graphene-COOH suspensions (1 ml, 2 ml, 4 ml, 6 ml) were activated with EDC (30 mg) and NHS (30 mg) in 1 ml water for 30 minutes and added to 10 ml of water-soluble chitosan solution (10 mg/ml) in water. The reaction was kept for 3 hours at room temperature before dialyzing in a 12 kDa molecular weight cutoff dialysis bag for 2 days at room temperature against water.

Finally, acrylated chitosan-graphene was prepared by adding 1 ml EDC and NHS activated acrylic acid to 10 ml of the above chitosan-graphene solution. After reacting for 3 hours, the solution was purified by dialysis in a 1 kDa molecular weight cutoff dialysis bag for 2 days at room temperature against water.

Preparation of the TPCG Hydrogel

The TPCG hydrogel was then prepared by adding 300 mg of NIPAM to 50 µl of PEGDA and 1 ml of acrylated chitosan-graphene (10 mg/ml) to 25 ml of nano-pure water in a three-necked flask. The solution was purged with argon gas for 30-45 seconds, and 25 ml of APS (53 mg in 25 ml) was added drop wise. The solution changed from colorless to white in 30 minutes and kept reacting for 4 hours. The sample solution was purified by dialysis in 1 kDa molecular weight cutoff dialysis bag for 2 days at room temperature against water. Some solution was kept at room temperature for a further thermal sensitivity test. The rest of the purified solution was freeze-dried and kept at 4° C.

Characterization of the TPCG Hydrogel

The particle morphology of the TPCG hydrogel was spherical and the particle size distribution was monodisperse (data not shown). UV-vis spectroscopy was used to analyze the optical absorption of TPCG compared to graphene. Similar to PEG-functionalized nanographene sheets [Yang, K. et al., Nano Letters (2010) 10, 3318], TPCG exhibited strong optical absorption (data not shown). Compared to the graphene, the apparent increase of absorption in the visible region (400-700 nm) was due to light scattering by the PNIPAM in the nanogel.

Figure 12A:
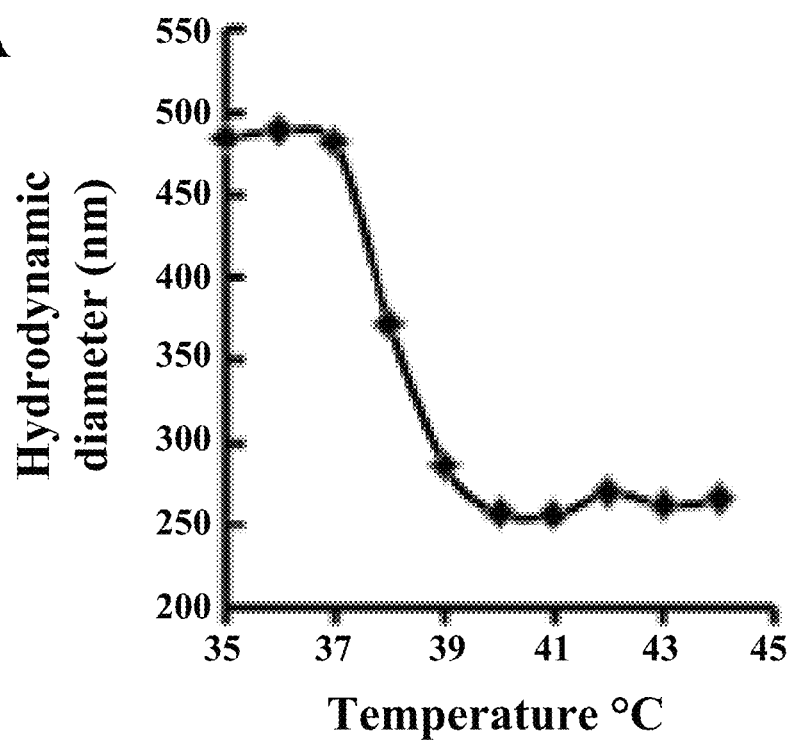
FIG. 12 (A-C) contains graphs showing (A) the temperature dependence of hydrodynamic diameter of TPCG; (B) absorbance at 650 nm of TPCG at various temperatures, insert shows the phase transition during temperature change; and (C) absorbance at 650 nm of TPCG after multiple heating/cooling steps.

The temperature-induced change in size of the TPCG was measured by DLS (FIG. 12A) using heat as the stimulus. The TPCG exhibited a thermoresponsive discontinuous phase-transition due to the dehydration of the polymer chains and the collapse of the hydrophilic segments. The diameter of TPCG decreased approximately 220 nm on heating to 40° C. The size of the dried TPCG (35 nm) observed in TEM was much smaller than the size determined by DLS.

The temperature dependence of the phase transition of TPCG was determined turbidimetrically (at 650 nm) by a Lambda 35 UV/vis spectroscopy (Perkin-Elmer, USA) fitted with a 1-cm optical path length quartz cell. The dispersions were diluted and heated from 35° C. to 45° C. at a heating rate of 1° C./minute. The hydrodynamic particle sizes of TPCG were measured from 35° C. to 42° C. using a DynaPro DLS plate reader (Wyatt Technology, Germany). The morphology of the TPCG was determined by transmission electron microscopy (TEM).

Figure 12B:
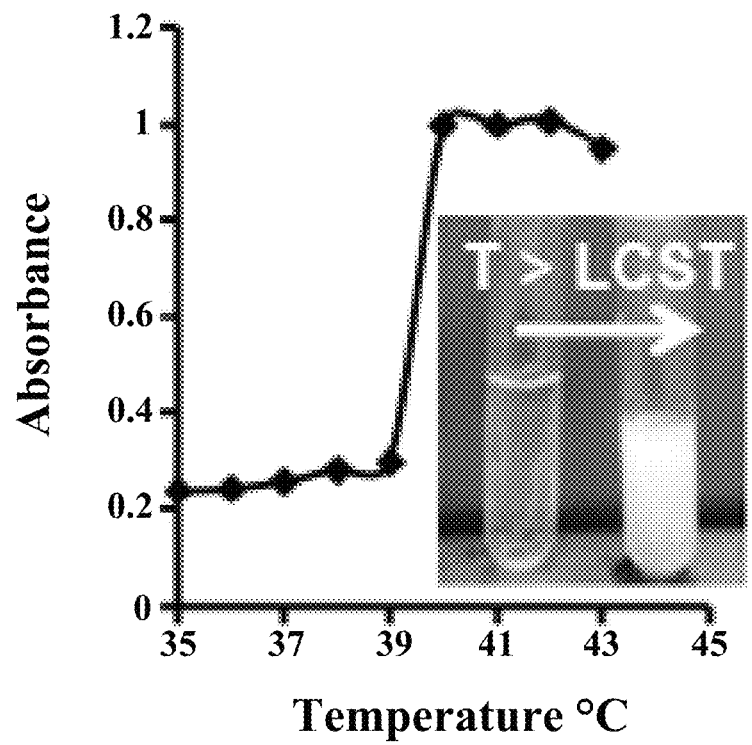
Figure 12C:
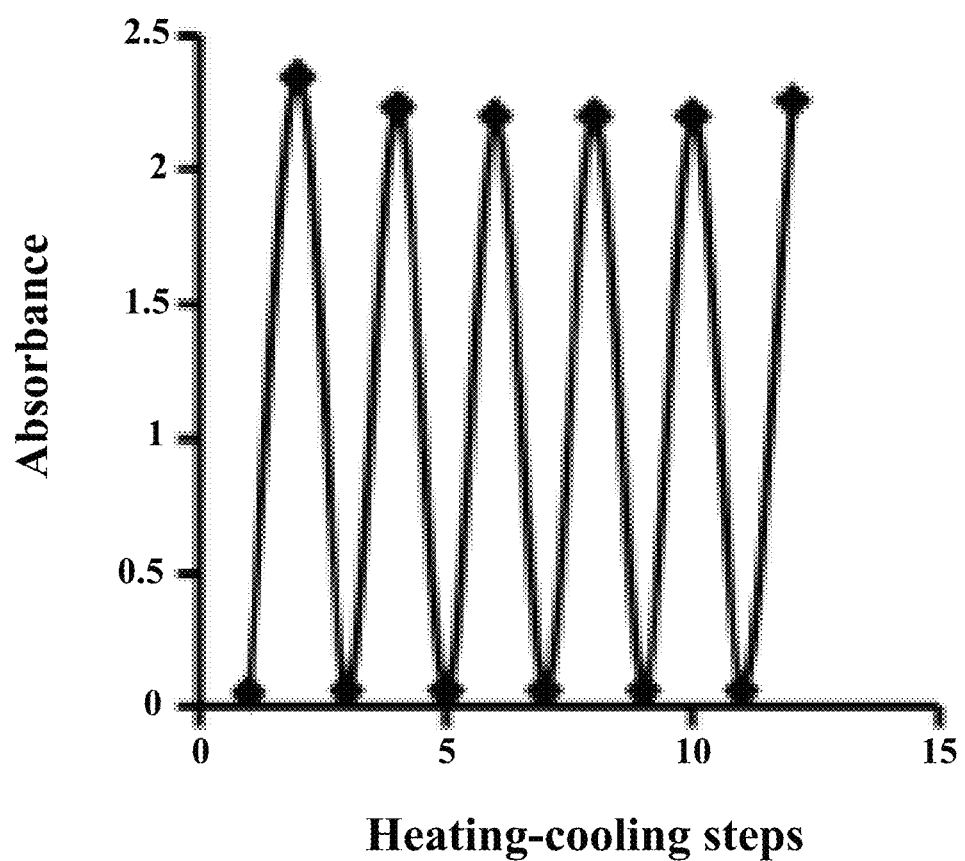

The thermosensitive behavior of TPCG at physiological temperatures was also evaluated by monitoring the turbidity change of aqueous TPCG solutions upon temperature change (FIG. 12B). The turbidity of TPCG solution increases rapidly with increasing temperature from 39° C. to 42° C. When the temperature reached 42° C., the nanogel began to shrink and water molecules were squeezed out of the nanogel. The difference in the refractive index between the nanogel and water increased, thus causing the increased turbidity. During cooling/heating cycles, the turbidity of the sample at 40° C. or 25° C. remained the same (FIG. 12C), suggesting that the turbidity changes with temperature were reversible.

Example 7

Cytotoxicity of TPCG Hydrogel

Figure 13:
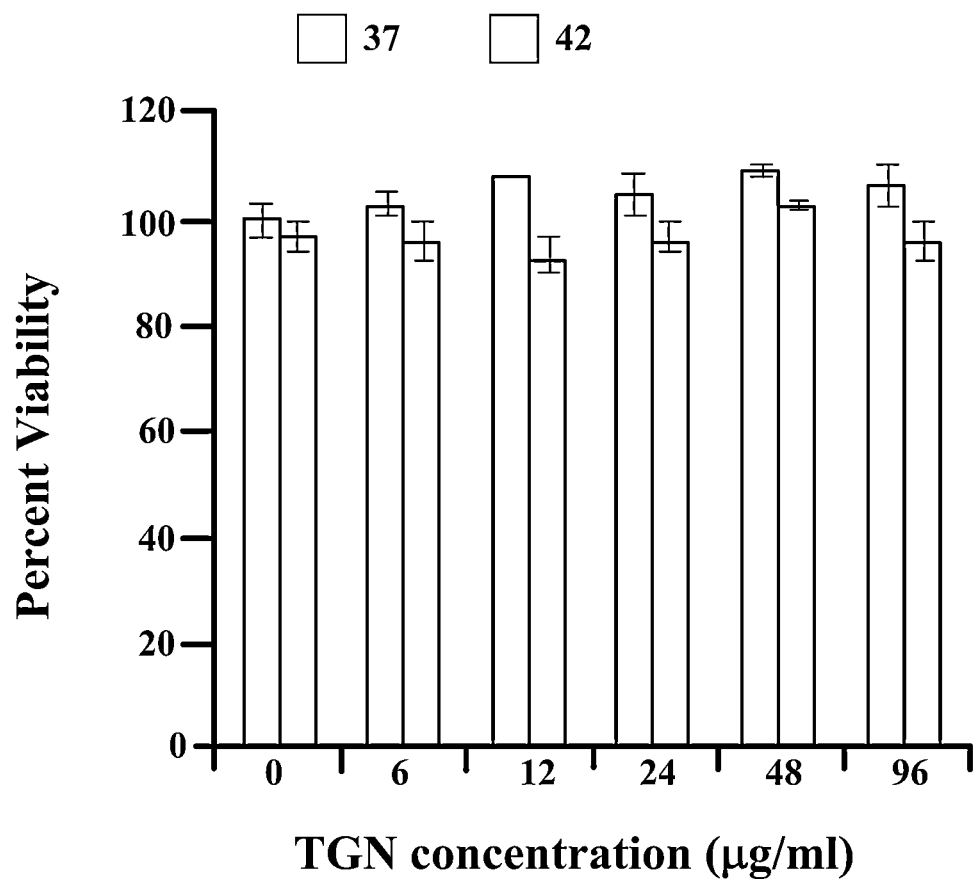
FIG. 13 is graph showing the viability of TRC1 cells treated with different concentrations of TPCG (referred to as TGN) at 37° C. for 72 hours, or 30 minutes at 42° C. then 37° C. for 72 hours.

To evaluate the potential application of this reversible thermal responsiveness of TPCG, its biocompatibility was assessed by testing the cytotoxicity of TPCG on a mouse prostate cancer cell line, TRC1. FIG. 13 shows the viability of TRC1 cells exposed to different concentrations of TPCG, expressed as a percent of cell survival without TPCG. There is no decrease in cell viability observed upon exposure to high concentration of TPCG. To test for possible effect of nanogel heating on cell viability, the cells were treated with different concentration of TPCG at 42° C. for 30 minutes and then returned to 37° C. The viability of cells incubated at 42° C. remained similar to those cultured at 37° C. (FIG. 13).

More specifically, TRC1 mouse prostate cancer cells were cultured in Dulbecco's modified Eagle's medium containing 4.5 g/L D-glucose, 110 mg/L sodium pyruvate, and 200 mM L-glutamine supplemented with 5% fetal bovine serum and 1% penicillin and streptomycin. In vitro cytotoxicity of TPCG was evaluated using the PrestoBlue® cell viability reagent (Life technology Frederick, Md.). Cells were seeded on 96-well plates (15,000 per well) and grown at 37° C. in a humidified atmosphere containing 5% $CO_2$ for 1 day to allow adherence. Various concentrations of TPCG were added to the wells in triplicate. The cells were cultured for 72 hours at 37° C. under 5% $CO_2$. After 72 hours, 10 μL of PrestoBlue reagent was added to each well and cells were incubated for 10 minutes. Cell viability was determined by measuring absorbance at 535 nm in a microplate reader (Synergy H4, Biotek). Cell viability (%) was calculated according to the following equation: Cell Viability (%)= (A535 sample)/(A535 control)×100.

Example 8

Drug Loading and Release of TPCG Hydrogel

For drug loading and release studies of the TPCG hydrogel, freeze-dried TPCG nanoparticles (1 mg) were mixed with different concentrations of DOX solution at 4° C. overnight. The solution was placed in a dialysis bag (1 kDa MWCO) against water to remove free DOX at room temperature for 2 hours. The dialysis bag with DOX loaded TPCG was placed into 30 ml phosphate-buffered saline (pH 7.4) in a 50 ml centrifuge tube. The tube was placed into a 37° C. water bath or a 45° C. water bath. At various times, 2 ml was withdrawn from the tubes to measure DOX absorption at 485 nm. The concentration of DOX was calculated from a standard curve of known DOX concentrations.

Figure 14A:
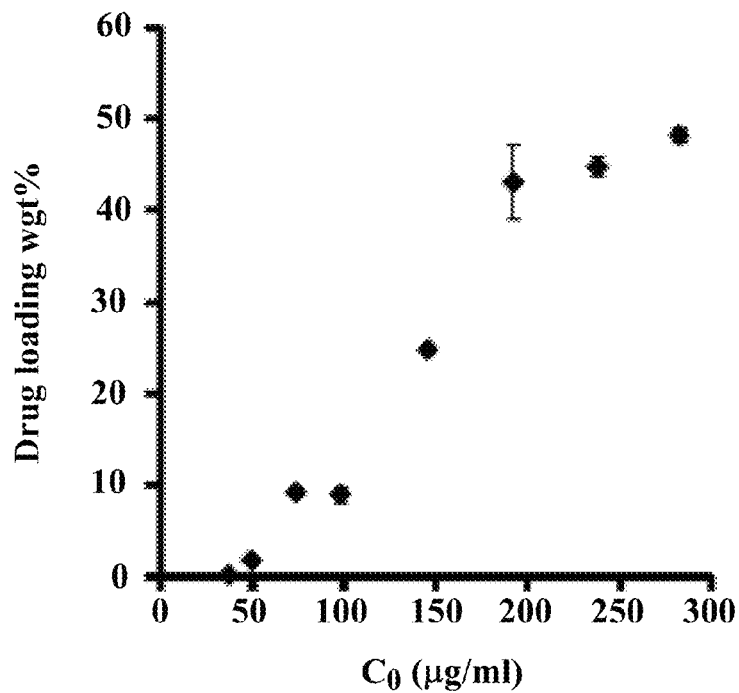
FIG. 14 (A-B) contains graphs showing (A) the drug loading as percentage of TPCG; (B) in vitro drug-release profiles from DOX-TPCG at pH 5.1 (♦) or pH 7.4 (■).
Figure 14B:
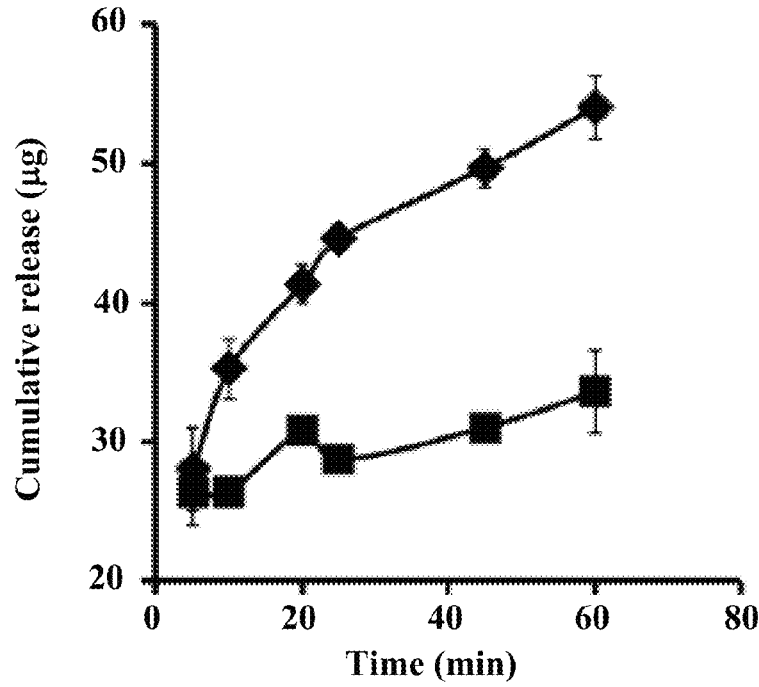

The drug loading content (wt %) at different DOX starting concentrations is shown in FIG. 14A. The drug loading content increased with DOX feeding concentration because more drug molecules were available for entrapment. The equilibrium drug loading content was found to be 48 wt % of dry TPCG. To determine how temperature influences the release of DOX, DOX-TPCG was incubated at 37° C. and 42° C. FIG. 14B shows the time-dependent release profile of DOX at 37° C. and 42° C.

Example 9

Cellular Uptake and Subcellular Localization of DOX-TPCG

To investigate the DOX release behavior of DOX-TPCG in cells at 37° C. and 42° C., TRC1 cells were treated with DOX-TPCG or free DOX (4 μM). For cellular uptake and subcellular localization tests, TRC1 cells were seeded (60,000 cells per chamber) in four-well chamber CellView™ culture dish (Griener, Bio-one) and grown at 37° C. overnight. The plates were put in 3i live cell pathology device at 37° C. or 42° C. After the samples (4 μM) were added to the cells, the fluorescent images were taken at 0 minutes, 30 minutes and 60 minutes with 3i Olympus Spinning Disk Confocal Microscope (laser, 488 nm).

At 37° C., both DOX-TPCG and free DOX were internalized into cells after 30 minutes. After 60 minutes, an increase in nuclear fluorescence intensity was observed for the free DOX. However, the DOX-TPCG showed fluorescence exclusively in the cytoplasm. In contrast, when the cells were incubated at 42° C. for 30 minutes, an increase in nuclear fluorescence intensity was observed for both free DOX and DOX-TPCG. At 37° C., DOX remained sequestered inside the nanogel after internalization of DOX-TPCG but DOX was released from the nanogel at 42° C. and entered the nucleus. Compared to 37° C., the cells show more internalization of both DOX-nanogel and free DOX at 42° C. (data not shown).

Example 10

Cytotoxicity of DOX-TPCG Against Cancer Cells in Culture

Figure 15A:
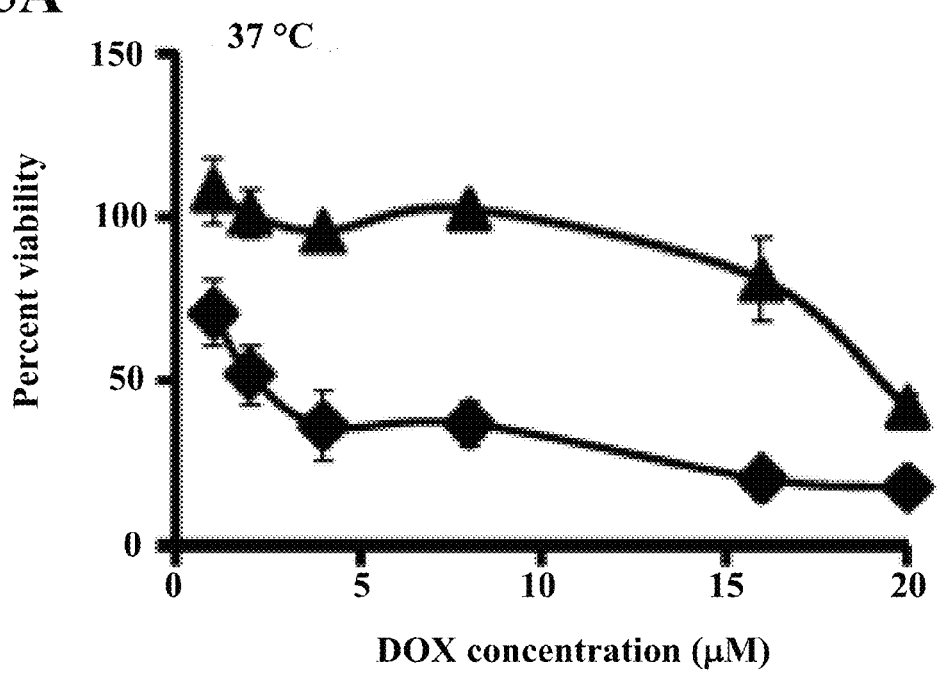
FIG. 15 (A-B) contains graphs showing the viability of TRC1 cells treated with different concentrations of DOX (♦) or DOX-TPCG (▲) at 37° C. for 72 hours (A), or 42° C. for 30 minutes then 37° C. for 72 hours (B).
Figure 15B:
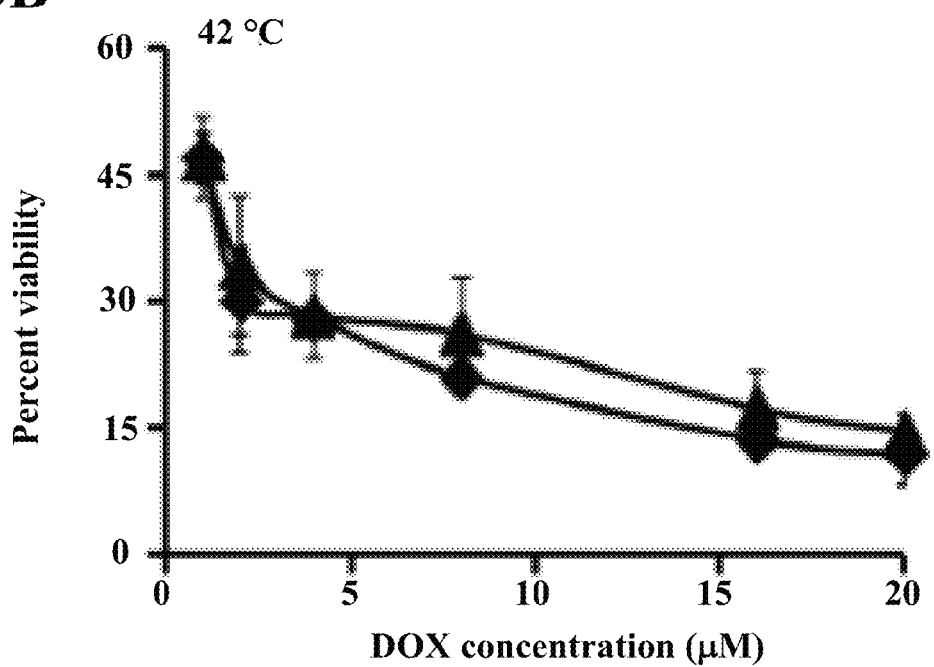

To determine the cytotoxicity of DOX-TPCG nanogels at 37° C. and 42° C., TRC1 cells were incubated with different concentrations of DOX-TPCG or free DOX at 37° C. for 72 hours (FIG. 15 A) or by incubating cells with different concentration of DOX-TPCG and free DOX at 42° C. for 30 minutes and then incubating them at 37° C. for 72 hours (FIG. 15B). More specifically, 15,000 cells per well were allowed to adhere to a 96-well plate overnight before adding DOX or DOX-TPCG. For testing the thermo-release of DOX from DOX-TPCG, the cells were incubated with DOX-TPCG or free DOX at 37° C. or 42° C. for 30 minutes after which the plates were returned to 37° C. for 3 days. The viability was determined by PrestoBlue assay as described above. Viability values were calculated as the fraction of treated cells/untreated cells.

At 37° C., the cytotoxicity of DOX-TPCG was significantly less than free DOX. The IC50 value of free DOX and DOX-TPCG were 2 μM and 20 μM, respectively. At 42° C., DOX-TPCG showed comparable cytotoxicity to free DOX. The IC50 of free DOX and DOX-TPCG was less than 1 μM.

The invention claimed is:

1. A hydrogel composition comprising:
   at least two acrylated chitosan-graphene monomers, where each chitosan-graphene monomer comprises:
   carboxylic acid functionalized graphene, where the chitosan component of the chitosan graphene-monomer is covalently bonded to the carboxylic acid functionalized graphene component of the chitosan-graphene monomer;
   and polyethylene (glycol) diacrylate (PEGDA), where the PEGDA covalently crosslinks the at least two acrylated chitosan-graphene monomers.

2. The hydrogel composition of claim 1, wherein the non-acrylated chitosan has a molecular weight of 10 kDa.

3. The hydrogel composition of claim 1, further comprising mesenchymal stem cells.

4. The hydrogel composition of claim 1, wherein the final weight percent of the functionalized graphene in the hydrogel is less than 0.1 percent.

5. The hydrogel composition of claim 1, wherein the final weight percent of the functionalized graphene in the hydrogel is 0.08 percent.

6. The hydrogel composition of claim 1, wherein the PEGDA is between 250 kDa to 6000 kDa.

7. The hydrogel composition of claim 1, further comprising N-Isopropylacrylamide (NIPAM), where the NIPAM is crosslinked at least one of the at least two acrylated chitosan-graphene monomers.

8. The hydrogel composition of claim 7, further comprising a pharmaceutical compound contained within the hydrogel.

9. The hydrogel composition of claim 8, wherein the pharmaceutical compound is doxorubicin.

10. The hydrogel composition of claim 8, wherein loading weight percent of the pharmaceutical compound in the hydrogel is between 27 wt % and 48 wt %.

11. The hydrogel composition of claim 7, wherein the hydrogel reversibly decreases in size at a temperature between 36° C. and 42° C.

12. The hydrogel composition of claim 7, wherein the hydrogel composition further comprises a pharmaceutical compound contained within the hydrogel and wherein the pharmaceutical composition is released from the when the hydrogel reversibly decreases in size at a temperature between 36° C. and 42° C.

13. A temperature responsive hydrogel composition comprising:
- at least two acrylated chitosan-graphene monomers, where each chitosan-graphene monomer comprises:
- carboxylic acid functionalized graphene, where the chitosan component of the chitosan graphene-monomer is covalently bonded to the carboxylic acid functionalized graphene component of the chitosan-graphene monomer;
- polyethylene (glycol) diacrylate (PEGDA), where the PEGDA covalently crosslinks the at least two acrylated chitosan-graphene monomers; and
- N-Isopropylacrylamide (NIPAM), where the NIPAM crosslinks at least one of the acrylated chitosan graphene monomers.

14. The temperature responsive hydrogel of claim 13, wherein the hydrogel is responsive to near infrared light.

15. The temperature responsive hydrogel of claim 13, wherein the hydrogel reversibly decreases in size at a temperature between 36° C. and 42° C.

16. The temperature responsive hydrogel of claim 13, further comprising a pharmaceutical compound contained within the hydrogel.

17. The temperature responsive hydrogel of claim 13, wherein the final weight percent of the functionalized graphene in the hydrogel is less than 0.1 percent.

18. The temperature responsive hydrogel of claim 13, wherein the hydrogel reversibly decreases in size at a temperature of 42° C.

19. The temperature responsive hydrogel of claim 13, further comprising a pharmaceutical compound contained within the hydrogel.

* * * * *